United States Patent
McMahon

(10) Patent No.: US 11,517,473 B2
(45) Date of Patent: Dec. 6, 2022

(54) MULTI-MODAL THERMAL THERAPY FOR BLEPHARITIS, MEIBOMIAN GLAND DYSFUNCTION AND DRY EYE SYNDROME

(71) Applicant: MG Therapies, Inc., Del Mar, CA (US)

(72) Inventor: David Michael McMahon, Del Mar, CA (US)

(73) Assignee: Solana Hesith, Inc., Del Mar, CA (US)

( * ) Notice: Subject to any disclaimer, the term of this patent is extended or adjusted under 35 U.S.C. 154(b) by 246 days.

(21) Appl. No.: 16/794,646

(22) Filed: Feb. 19, 2020

(65) Prior Publication Data

US 2020/0188169 A1    Jun. 18, 2020

Related U.S. Application Data

(63) Continuation-in-part of application No. 16/111,859, filed on Aug. 24, 2018, now abandoned.

(60) Provisional application No. 62/807,572, filed on Feb. 19, 2019, provisional application No. 62/550,655, filed on Aug. 27, 2017.

(51) Int. Cl.
*A61F 7/00* (2006.01)
*A61F 9/007* (2006.01)
*A61H 7/00* (2006.01)
*A61H 5/00* (2006.01)

(52) U.S. Cl.
CPC ............ *A61F 9/00718* (2013.01); *A61F 7/00* (2013.01); *A61H 7/003* (2013.01); *A61F 2007/0004* (2013.01); *A61F 2007/0086* (2013.01); *A61F 2007/0087* (2013.01); *A61H 2201/0153* (2013.01); *A61H 2201/0207* (2013.01); *A61H 2201/0285* (2013.01); *A61H 2201/10* (2013.01); *A61H 2201/5007* (2013.01);
(Continued)

(58) Field of Classification Search
CPC ................ A61F 7/00; A61F 2007/0004; A61F 2007/0086; A61F 2007/0087; A61H 2205/024; A61H 2201/0153; A61H 2201/0207; A61H 2201/10; A61H 2201/5082
See application file for complete search history.

(56) References Cited

U.S. PATENT DOCUMENTS 4,308,013 A  12/1981 Major
5,097,828 A   3/1992 Deutsch
(Continued)

OTHER PUBLICATIONS

PCT/US2018/048001 Written Opinion ISR, dated Oct. 22, 2018.

*Primary Examiner* — Kaitlyn E Smith
*Assistant Examiner* — Annie L Patton
(74) *Attorney, Agent, or Firm* — Richard Batt

(57) ABSTRACT

Methods for treating Blepharitis, Meibomian Gland Dysfunction and Dry Eye Syndrome include thermal massage, thermal debridement, and thermal expression. Particular embodiments include use of handheld devices that provide the thermal therapy to tissue by contacting a surface heated with thermal energy to a patient's tissue. Thermal energy can be continuously provided during operation. In particular embodiments, a handheld device comprises a base assembly operatively connected to a removeable thermal energy applicator. A wide range of thermal applicators may be connected to the base assembly to provide different treatments, including heat application, debridement, and expression of the treated tissue or gland.

16 Claims, 17 Drawing Sheets

(52) U.S. Cl.
CPC ............... *A61H 2201/5043* (2013.01); *A61H 2201/5082* (2013.01); *A61H 2205/024* (2013.01)

(56) References Cited

U.S. PATENT DOCUMENTS

| | | | |
|---|---|---|---|
| 5,573,529 A | 11/1996 | Haak et al. | |
| 5,618,274 A | 4/1997 | Rosenthal | |
| 5,830,208 A | 11/1998 | Muller | |
| 6,047,215 A | 4/2000 | McClure et al. | |
| 6,436,113 B1 | 8/2002 | Burba et al. | |
| 6,679,908 B2 | 1/2004 | Shimizu | |
| 7,120,488 B2 | 10/2006 | Nova et al. | |
| 7,231,922 B2 | 6/2007 | Davison et al. | |
| 8,491,505 B2 | 7/2013 | Yang | |
| 8,523,791 B2 | 9/2013 | Castel | |
| 8,613,762 B2 | 12/2013 | Bledsoe | |
| 8,721,572 B1 * | 5/2014 | Linder | A61H 15/0078 601/15 |
| 8,758,419 B1 | 6/2014 | Berry et al. | |
| 8,876,859 B2 | 11/2014 | Buehler et al. | |
| 9,763,827 B2 | 9/2017 | Kelleher et al. | |
| 9,956,355 B2 | 5/2018 | Besirli et al. | |
| 10,130,507 B2 | 11/2018 | Whitehurst et al. | |
| 2001/0007952 A1 | 7/2001 | Shimizu | |
| 2002/0087179 A1 | 7/2002 | Culp et al. | |
| 2004/0068309 A1 | 4/2004 | Edelman | |
| 2007/0060988 A1 | 3/2007 | Grenon et al. | |
| 2008/0046047 A1 | 2/2008 | Jacobs | |
| 2008/0046048 A1 | 2/2008 | Grenon et al. | |
| 2008/0109052 A1 * | 5/2008 | Grenon | A61N 5/025 607/104 |
| 2008/0109053 A1 | 5/2008 | Grenon et al. | |
| 2008/0228248 A1 | 9/2008 | Guyuron et al. | |
| 2010/0016933 A1 | 1/2010 | Chen et al. | |
| 2012/0165908 A1 | 6/2012 | Kou et al. | |
| 2012/0209154 A1 | 8/2012 | Williams, III et al. | |
| 2012/0239122 A1 | 9/2012 | Dong et al. | |
| 2013/0085552 A1 | 4/2013 | Mandel | |
| 2013/0184693 A1 | 7/2013 | Neev | |
| 2013/0281851 A1 | 10/2013 | Carr | |
| 2014/0200487 A1 | 7/2014 | Ramdas et al. | |
| 2014/0249455 A1 | 9/2014 | Parish et al. | |
| 2015/0005750 A1 * | 1/2015 | Kelleher | A61N 5/0625 606/3 |
| 2015/0032059 A1 | 1/2015 | Allerdings et al. | |
| 2015/0056095 A1 | 2/2015 | Gorzen et al. | |
| 2015/0057701 A1 | 2/2015 | Kelleher et al. | |
| 2015/0157347 A1 | 6/2015 | Grenon et al. | |
| 2015/0157530 A1 | 6/2015 | Soriano | |
| 2015/0216722 A1 * | 8/2015 | Choate | A61F 9/00772 606/162 |
| 2015/0216725 A1 * | 8/2015 | Korb | A61F 9/00718 606/171 |
| 2015/0272623 A1 | 10/2015 | Ignon et al. | |
| 2015/0283402 A1 | 10/2015 | Grenon et al. | |
| 2015/0320590 A1 | 11/2015 | Whitehurst et al. | |
| 2015/0366703 A1 | 12/2015 | Du | |
| 2016/0243000 A1 | 8/2016 | Gray et al. | |
| 2016/0317379 A1 | 11/2016 | Mosaddegh | |
| 2017/0087009 A1 * | 3/2017 | Badawi | A61F 7/007 |
| 2017/0273823 A1 | 9/2017 | Novkov et al. | |
| 2019/0060115 A1 | 2/2019 | Novkov et al. | |
| 2019/0307606 A1 * | 10/2019 | Andino | A61F 9/0017 |
| 2020/0069468 A1 * | 3/2020 | Litherland | A61F 7/00 |
| 2020/0188169 A1 | 6/2020 | McMahon | |

* cited by examiner

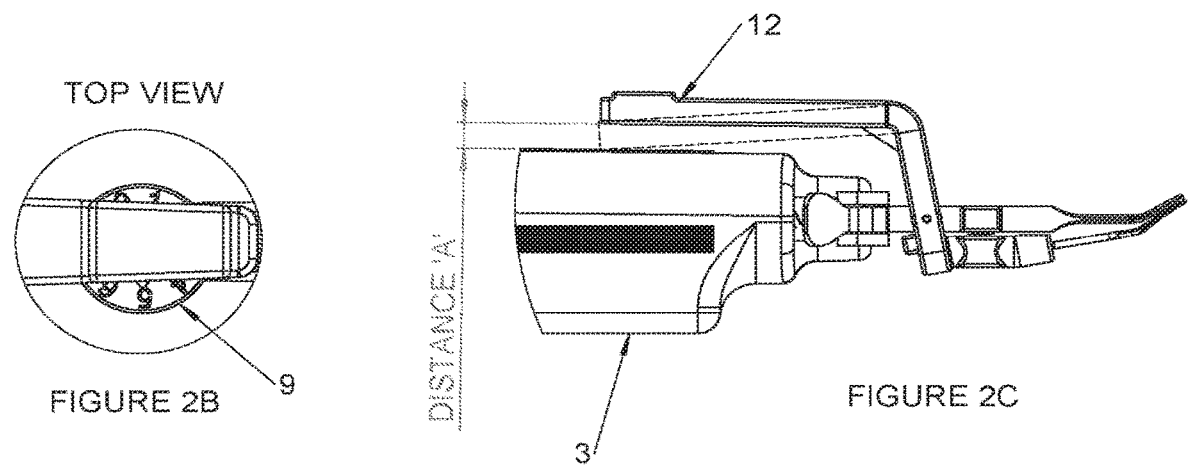
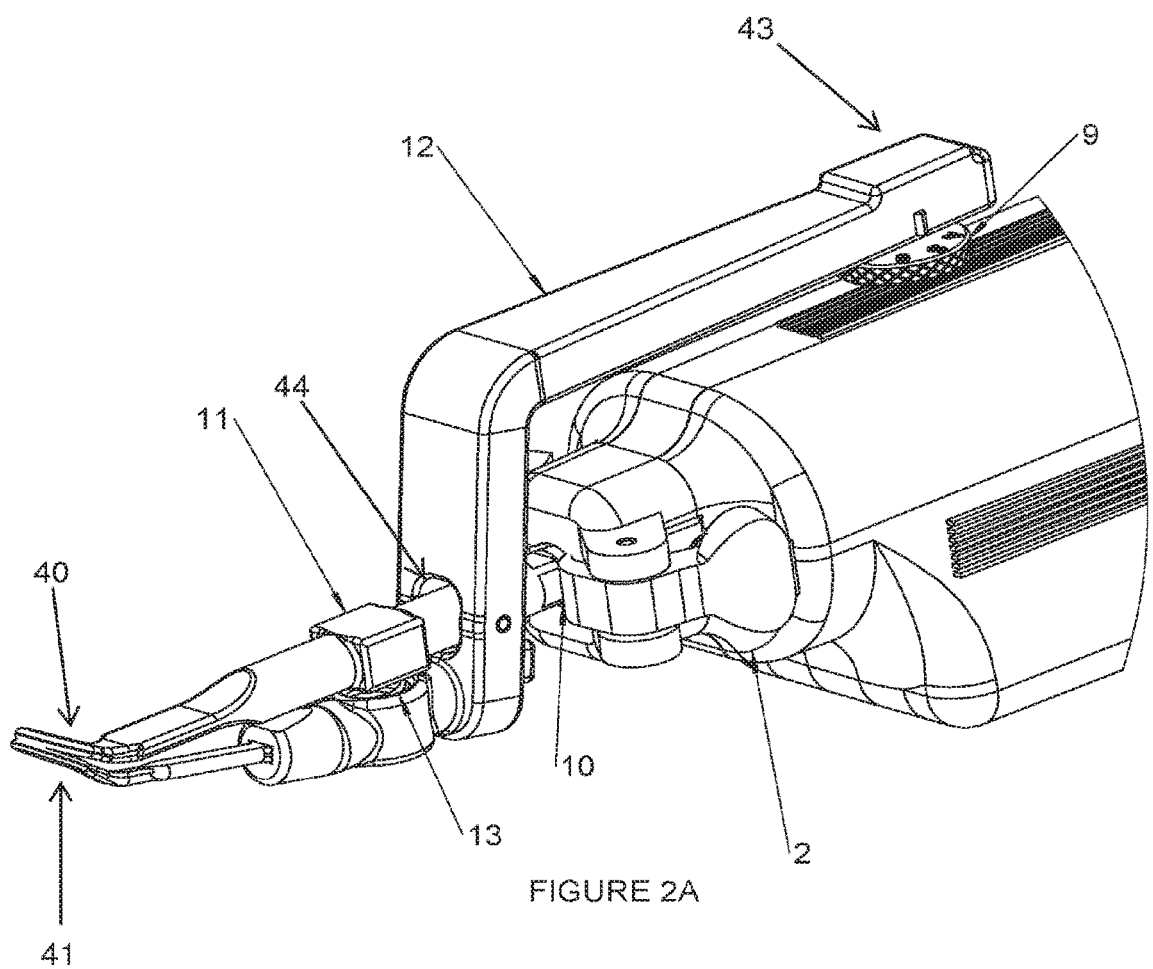

HEAT FLOW

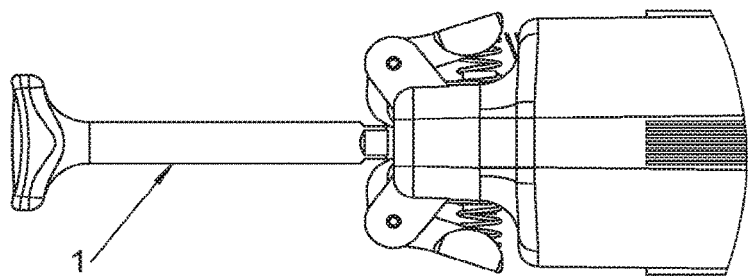
FIGURE 4A
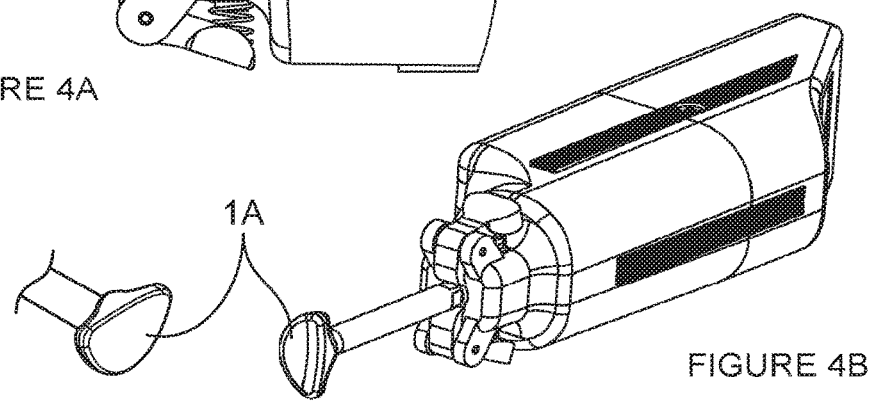
FIGURE 4B
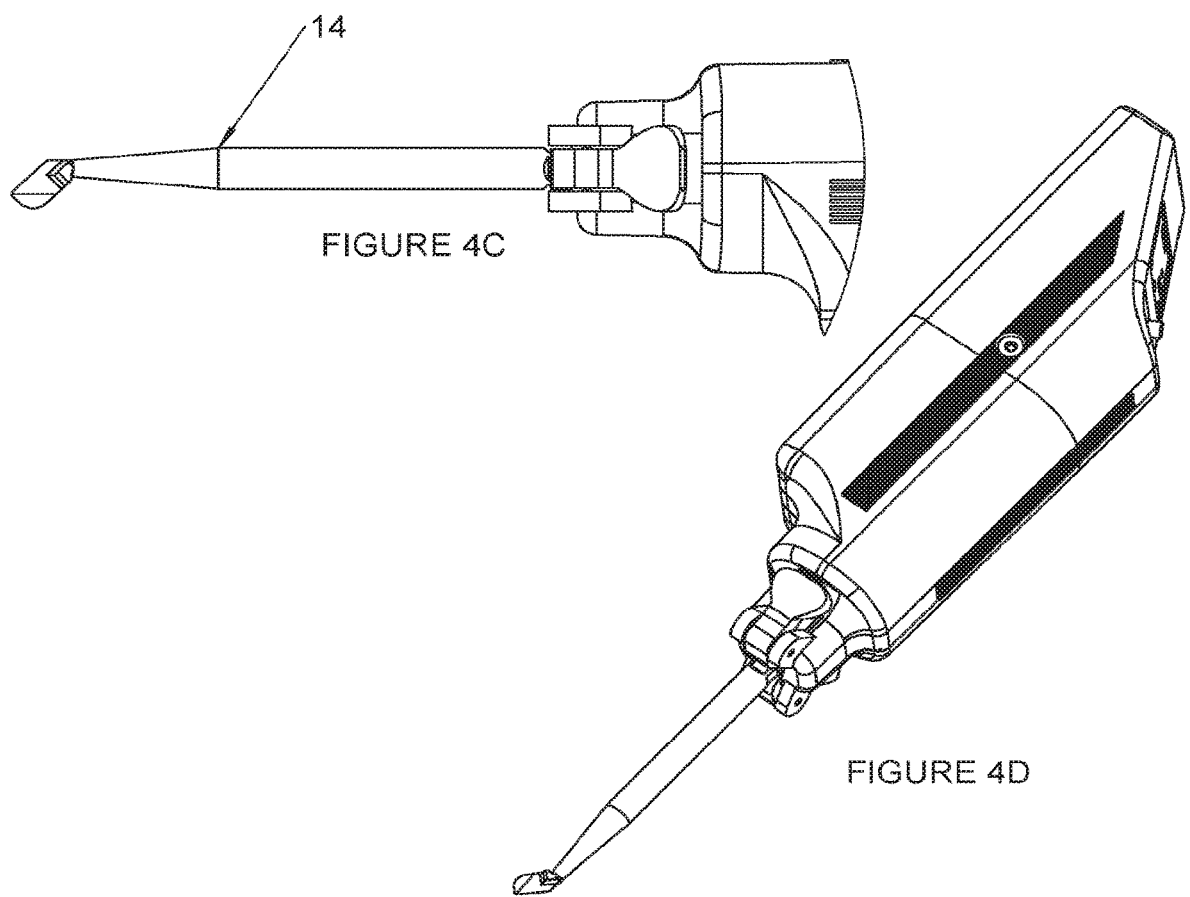
FIGURE 4C
FIGURE 4D

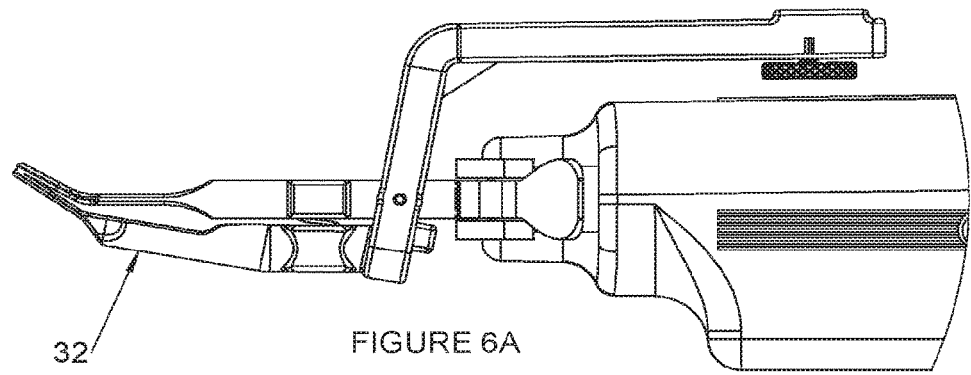
FIGURE 6A
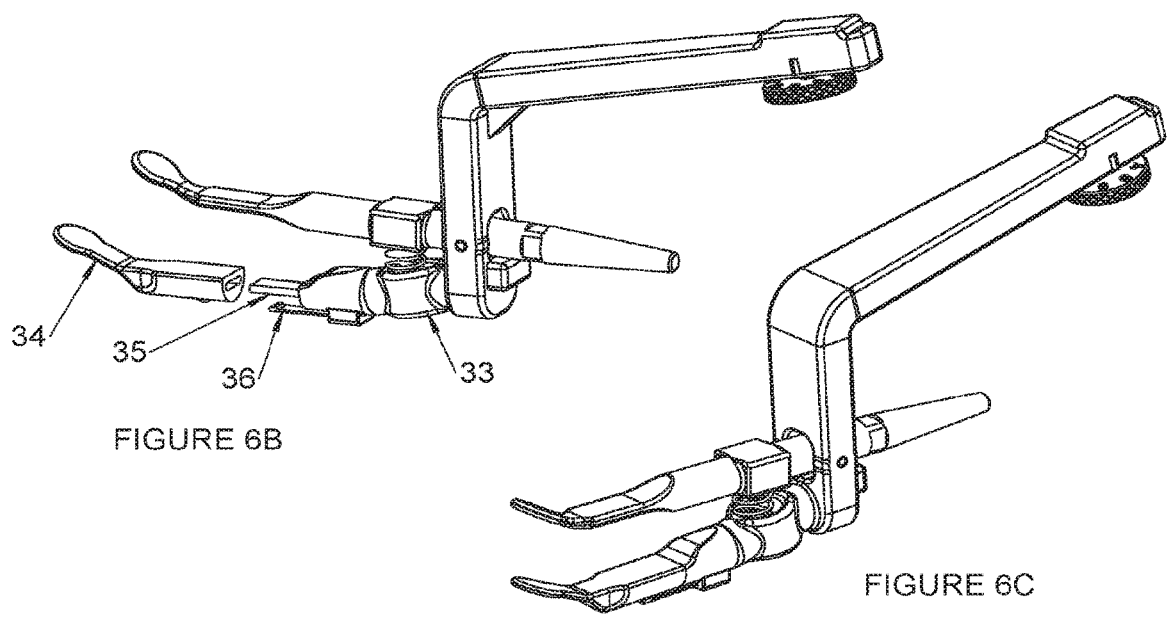
FIGURE 6B
FIGURE 6C
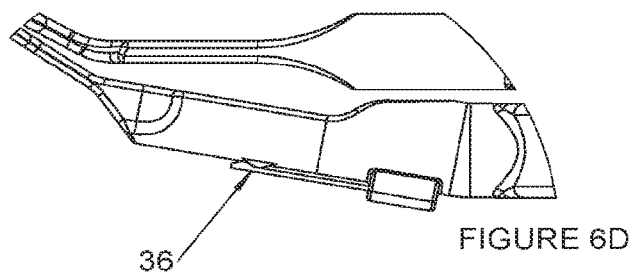
FIGURE 6D

MULTI-MODAL THERMAL THERAPY FOR BLEPHARITIS, MEIBOMIAN GLAND DYSFUNCTION AND DRY EYE SYNDROME

CROSS-REFERENCE TO RELATED APPLICATIONS

This application claims the benefit of U.S. Provisional Application No. 62/807,572, filed Feb. 19, 2019, and is a continuation in part application of U.S. application Ser. No. 16/111,859, filed Aug. 24, 2018, which claims the benefit of priority of U.S. Provisional Application No. 62/550,655, filed Aug. 27, 2017, the entire contents of each being incorporated herein by reference in its entirety for all purposes.

BACKGROUND OF THE INVENTION

Field of the Invention

This application is directed to providing thermal therapy for patients to treat dry eyes. In particular, methods are described for providing thermal therapy to a patient's eyelid for the treatment of Meibomian Gland Dysfunction (MGD), Blepharitis, and Dry Eye Syndrome (DES).

Description of the Related Technology

The leading causes of dry eyes are Blepharitis, in particular Posterior Blepharitis and dysfunction of the meibomian glands, also known as Meibomian Gland Dysfunction (MGD).

Blepharitis is defined as inflammation of the eyelids. Posterior Blepharitis involves inflammation of the Meibomian Glands and is marked by oily, gritty, or foamy discharge from the Meibomian Glands.

With reference to FIG. 1A, Blepharitis most commonly occurs when tiny oil glands 62 (namely, the meibomian glands) located on the posterior edge 61 of the lid margin are inflamed and become clogged. This leads to irritated and red eyes. Blepharitis is often a chronic condition that is difficult to treat. Blepharitis can be uncomfortable and may be unsightly.

Meibomian gland dysfunction (MGD) is when blockage or some other abnormality of the meibomian glands 62 in the lower and upper eyelids 64,65 prevent secretion of meibum to the surface of the eye. Although MGD can include cases of either hypersecretion of meibum or hyposecretion, most cases of MGD and blepharitis involve blockage and obstruction of the meibomian glands, with associated decreased secretion of meibum.

This is undesirable because meibum is a key component to keep the lipid tear layer in contact with the surface of the eye and its absence leads to inappropriate evaporation of tears from the eye surface and hence dry eye results.

There is no consensus on the optimal means of treating dry eye due to MGD and blepharitis. The ultimate goal is to restore meibum secretion and improve dry eye symptoms. To achieve this, a diverse set of treatments exist, including massage, heat, antibiotics, and anti-inflammatories is currently used. The algorithm for managing Blepharitis and MGD in these patients usually begins with eyelid hygiene—patients massage the eyelids, often after applying heat or warm compresses, and then attempting to clean the eyelid with mild soaps. If this is ineffective, artificial tears, lubricants, antibiotics, anti-inflammatories, lipid diet supplements, cyclosporine and rarely surgery can be indicated.

In addition to eyelid hygiene, a number of thermal therapy devices exist for treating MGD including the MiBo Thermoflo device manufactured by MIBO Medical Group (Dallas, Tex.) and the LipiFlow Thermal Pulsation System manufactured by Johnson & Johnson (Morrisville, N.C.).

However, each of the above-mentioned thermal therapy devices applies only one treatment modality. Particularly, the MiBo Thermoflo device applies only heated massage and the LipiFlow Thermal Pulsation System applies only thermal pulsation. Additionally, and perhaps more importantly, neither of the above-mentioned devices enables a user to debride the eye lid margin.

The invention disclosed herein addresses the problems stated above as well as other existing problems in the art of multi-modal treatment for Blepharitis, MGD and DES.

Described herein is a novel, multi-modal thermal device (MMTD) and related methods for treating Blepharitis, MGD and DES.

SUMMARY OF THE INVENTION

A method, system, and apparatus include one or more thermal modalities for treating dry eyes, and in particular embodiments, for treating Blepharitis, Meibomian Gland Dysfunction and Dry Eye Syndrome.

In embodiments, a method applies heat to the exterior of the eyelid; debrides the eyelid while simultaneously applying heat to decap the glands; and applies opposing forces to the interior and exterior of the eyelid while simultaneously applying heat to express the meibum.

In embodiments, the step of applying heat to the exterior of the eyelid may be performed by applying heat alone, heat and moisture, heat and pressure or a combination of any aforementioned.

In embodiments, the heating step can be performed using a handheld instrument.

In embodiments, the heating step can be performed using a heated compress. Heating the compress may be carried out in various ways such as by microwave, electronically via USB port and powered by a portable battery, or another energy source.

In embodiments, during the debriding step, the debriding is carried out on the eyelid posterior margin.

In embodiments, during the thermal expression step, heat is applied only to the exterior side of the eyelid, and not applied to the inner side of the eyelid.

In embodiments, during the thermal expression step, heat is applied to the exterior side of the eyelid and to the inner side of the eyelid.

In embodiments, during the thermal expression step, the opposing forces to the eyelid are limited and controlled so as to reduce the risk of scarring or damage to the Meibomian glands or eye lids.

In embodiments, during the thermal expression step, the pressure applied to the inner side of the eyelid is performed by an elastic member, deforming or conforming to some degree as increased pressure is applied to the inner eyelid thereby avoiding trauma to the eyelid.

In embodiments, the thermal expression is performed by opposing paddles. The diameter of the paddle surface area may vary. In particular embodiments, the diameter of a paddle surface area is 5-10 mm, and more preferably 6-9 mm, and most preferably about 8 mm.

In embodiments, the step of thermal expression of the upper and lower eye lids is performed under a pressure range not exceeding a predetermined maximum pressure. In embodiments, the predetermined maximum pressure ranges from 5 to 50 PSI, and in one particular embodiment pressure is limited to not exceed a maximum of 35 PSI.

In embodiments, the opposing forces during the thermal expression clamp/squeeze the eyelid from a first thickness to a second thickness, and the method prohibits the second thickness from being less than a predetermined threshold thickness. In embodiments, the predetermined threshold thickness ranges from 0.2 mm to 1.5 mm.

In embodiments, the time for performing thermal expression on an eyelid ranges from 30 seconds-3 minutes.

In embodiments, the step of thermal debriding is performed prior to the step of thermal expression.

In embodiments, the step of thermal exterior eyelid heating is performed prior to the step of thermal debridement. In embodiments, the time for performing thermal massage is from 1-10 minutes, and in one embodiment less than 5 minutes, and in one particular embodiment 1-2 minutes.

In embodiments, the temperature of the thermal exterior eyelid heating is 40 to 50 degrees C., and in one embodiment is less than or equal to 43 degrees C.

In embodiments, a medical device delivers thermal therapy to tissue, and in particular embodiments is adapted to deliver thermal energy to the eyelid.

In embodiments, a multi-modality therapy device (MMTD) has three modes of action: Thermal External Lid Heating, thermal Lid Debridement, and a thermal Meibomian Gland Expression mode. An MMTD is preferably configured as a hand-held cordless device, is rechargeable, reusable, and enables the use of at least three different detachable instruments (or applicators) each of which is adapted to deliver a unique mode of treatment. Instruments and modes can be changed with the push of a button by replacing one applicator for another applicator.

In embodiments, the device and instrument have a lock and key arrangement/design in which an elongate ridge or tongue on the instrument locates (both axially and rotationally) the instrument into the handle assembly's loading channel such that the instrument cannot be misloaded. Additionally, in embodiments, the instrument is secured with a spring-loaded locking mechanism in the handle such as a tab that registers with a notch or detent in the instrument.

In embodiments, the instruments are designed to be autoclaved and are reusable. In embodiments, the MMTD weighs less than 10 ounces (e.g., about 6 ounces) and is ergonomically easy to use. In embodiments, the device is rechargeable, and in one embodiment, is adapted such that one charge allows for multiple patient treatments.

In embodiments, the present invention includes a processor such as a microprocessor or analog circuit-controlled device that is handheld and powered by either an internal battery and optionally cordless, or a cable that is connected to an external power source. The device is used to deliver several thermal therapies/treatments to a patient's tissue surface including eye surfaces using various interchangeable thermally-conductive metal thermal energy applicators (instruments) that are heated to various temperatures and in some cases enable compression of tissue by the user's mechanical action. When used to treat eyelids, the eyelid margin and more specifically the Meibomian glands may be treated in order to express fluid and contents from the Meibomian glands.

In embodiments, a method includes the treatment of Meibomian Gland Dysfunction (MGD), or posterior blepharitis; a common physiological ailment related to the lack of proper flow of Meibomian gland secretions, resulting in a condition known as Dry Eye Disease (DED). The present invention enables a clinician to conduct these treatments using actively heated instruments that apply specific heat to the patient-contacting surfaces only, along with thermal massage of the eyelid surfaces prior to these treatments using a Thermal Massage Instrument.

In embodiments, a method provides active heating. Actively heating the eyelid allows heat energy to be transferred into the patient-contacting surface constantly during the procedure in order to maintain approximately constant temperature at that surface and thus obtain optimum results.

In embodiments, temperature can be selected by the user. Embodiments allow for user selectable temperature set points. The embodiment shown allows the user to select any of the available different treatments, each with a specific pre-programmed set point temperature that has been clinically determined to be optimum for the specific therapy/treatment. Further embodiments may include more or less discrete set points. Yet further embodiments may allow for a continuously adjustable set point within a given temperature range. The internal control system of the device regulates the heating element in order to control the temperature at the patient side of the instrument part based on measurement of the conductive metal temperature on a surface close to the heating element, or more preferably spaced from the heating element and close to the tissue contacting surface of the instrument head. In embodiments, an empirical algorithm based on test data or a theoretical algorithm is used to adjust the control temperature to whatever is required in order to obtain the set point temperature at the patient-contacting surface of the instrument part.

In embodiments, a system for providing thermal therapy comprises: heater power electronics to control heat generation; microprocessor electronics to control a heating element, user interaction, and device communication; a heating element positioned for operative connection with a thermal energy applicator; a removeable thermal energy applicator comprised of at least one contact surface configured to communicate thermal energy between the applicator and the patient's tissue, the removable thermal energy applicator is configured to securely connect to the housing; and a heat flow adapter configured to operatively connect to the removable thermal energy applicator and the heating element at the adapter-applicator interface; wherein the heater power electronics, the microprocessor electronics, and the heating element are housed in a housing.

In embodiments, the heating element is a resistive heating pad, a thermoelectric cooler, a resistive heating blanket, or a coil of resistance wire. Preferably, the heating element is insulated to increase heating efficiency and to prevent wear or excess heat on other components within the handle assembly.

In embodiments, the removable thermal energy applicator comprises a contact surface oriented orthogonally with respect to the body of the applicator.

In embodiments, the removable thermal energy applicator comprises a debridement tool, preferably having a bladed or sharp tip for scraping the biofilm off the eyelid.

In embodiments, the removable thermal energy applicator comprises two thermal rollers.

In embodiments, one of the thermal rollers is heated and the other is non-heated, and wherein the non-heated roller is made of metal or soft material such as plastic or elastomer.

In embodiments, the non-heated roller is detachable from the remainder of the removable thermal energy applicator.

In embodiments, pressure exerted to tissue being compressed between two rollers is limited by a physical stop or other mechanisms such as a collapsing leaf spring that fails under a prescribed pressure load such that additional force cannot be applied, adjustable spring to limit the amount of pressure exerted on the tissue being treated in order to reduce or eliminate the risk of causing scarring or other damage to the tissue.

In embodiments, the removable thermal energy applicator comprises two paddles acting as contact surfaces.

In embodiments, both paddles are thermally controlled.

In embodiments, one paddle is heated and the other paddle is non-heated, and wherein the non-heated paddle is made of metal, plastic or elastomer.

In embodiments, the non-heated paddle is detachable from the remainder of the removable thermal energy applicator.

In embodiments, pressure exerted to tissue being compressed between two paddles is limited by a physical stop or other mechanisms such as adjustable spring to limit the amount of pressure exerted on the tissue being treated in order to reduce or eliminate the risk of causing scarring or other damage to the tissue.

In embodiments, the system is configured to operatively communicate with a remote computing device.

In embodiments, the remote computing device is configured to track operating parameters of the device and output usage information for general data collection, use in clinical treatment, or monetarily charge of the users.

In embodiments, the remote computing device is further configured to communicate with a third-party computing device and receive information from the third-party computing device to control the device.

In embodiments, the system further comprises a battery housing to contain a battery and battery charging and load sharing electronics.

In embodiments, the system further comprises a thermal cut out device to serve as a fuse.

In embodiments, the system further comprises a USB connector for power provision and communication with the microprocessor for software loading.

In embodiments, the system further comprises a graphical display for displaying information relating to the use of the system.

In embodiments, the graphical display is LED, OLED, or LCD display.

In embodiments, the graphical display allows for user interface with the display.

In embodiments, the system further comprises a temperature sensor operatively connected to measure temperature created by the heating element and configured to communicate temperature measurements to the microprocessor electronics.

In embodiments, a processor (optionally, a microprocessor) is operable or programmed with a compensating algorithm (e.g., a set of computer readable instructions stored in a local non-transient memory device) to continuously adjust the temperature of the instrument at the patient contacting surface to maintain a set temperature based on frequent measurements of the instrument temperature at or near the patient/tissue contacting surface. Use of this 'tip local' temperature to adjust the set temperature of the instrument serves to compensate for heat sink from the patient's tissue, changes in ambient air temperature, and variations in the instrument temperature itself (e.g., if a cold or hot instrument is inserted into the device) which a mere measurement of the heat element or measurement of a heating block used to transfer heat to a patient contacting instrument alone would not mitigate.

In embodiments, the temperature near the tissue contact surface is measured many times per second, optionally, 100 or 1,000 times or more per second, or continuously.

In embodiments, the power is adjusted to the heating element many times per second, optionally, 20 hertz (namely, 20 times per second) or more, or continuously.

In embodiments, the processor is operable to execute an instrument detection algorithm that identifies the type of instrument loaded into the handpiece based on a heat signature (namely, a temperature time profile) response. The heat signature can be generated variously and in embodiments, the heat signature is generated by applying in advance a constant power to each type of instrument and recording the temperature versus time. Without intending to being bound to theory, the temperature is a function of instrument mass and heat capacity. Each type of instrument in the subject invention has a unique thermal footprint such that a score or signature or profile can be correlated with a specific type of instrument.

In embodiments, the processor is operable to automatically activate a heating mode (e.g., massage, debridement, expression) and the corresponding pre-determined set-temperature for each mode and in some embodiments, the corresponding pre-determined temperature and procedure time, and in other embodiments, a pre-determined varying temperatures function of time.

In embodiments, the processor is operable to determine whether an instrument is not loaded properly, the wrong instrument is loaded or no instrument is loaded. The 'No Instrument Detection' algorithm is based on measured temperature time profile when heat is applied to the heating element. Optionally, the processor determines whether to send an alert to the user (e.g., via audible and visual alarms) in the case that no instrument has been installed within a threshold time period (e.g., 1 minute) after a treatment mode has been selected. Preferably, the processor is operable to automatically turn off heating, and returns the device to a neutral state, requiring the user to physically act to turn off alarms (e.g., by pushing the mode button described further herein).

In embodiments, a kit for treating conditions of the eye comprises a portable thermal generation device and a set of different types of thermal applicators, and optionally one-piece thermal applicators. Each thermal applicator comprises: a distal head selected from the group consisting of an expression face, debridement face, and massage face, each of which is adapted to contact the eyelid of a patient.

Each type of thermal applicator also includes a universal proximal end adapted to removably engage with the portable thermal generation device to enable heat to be applied from the portable thermal generation device, to the distal head to the eyelid.

In embodiments, the portable thermal generation device further comprises a temperature capture assembly spaced distally from a heat element in the portable thermal generation device. The temperature capture assembly preferably has a channel or groove defined therein, and a temperature sensor in thermal contact with the groove. The groove is sized to receive and thermally connect with an elongate universal ridge on each of the types of thermal applicators.

In embodiments, the portable thermal generation device further comprises a processor operable to determine whether a thermal applicator is correctly installed based on data received from the temperature capture assembly. The processor also can be operable to determine which type of thermal applicator is installed based on information from the temperature capture assembly.

In embodiments, the processor is further operable to determine a candidate thermal mode corresponding to the type of thermal applicator installed, and to run the thermal candidate mode or, if a selected mode was selected by the user, to compare the candidate mode to the selected mode and run the selected mode only if the candidate mode and selected mode match to a sufficient level.

BRIEF DESCRIPTION OF THE DRAWINGS

FIG. 2A shows an isometric view with the regular Expression Instrument installed.

FIG. 2B shows an embodiment with a Thumb Wheel compression force adjustment.

FIG. 2C shows an embodiment with the compression force being limited by a hard stop.

FIGS. 4A and 4B show the Thermal Massage Instrument installed.

FIGS. 4C and 4D show the Debridement Instrument installed.

FIG. 6A shows the Atraumatic Expression Instrument installed.

FIGS. 6B, 6C and 6D show the separable Atraumatic Expression Instrument installed.

DETAILED DESCRIPTION

Figure 1A:
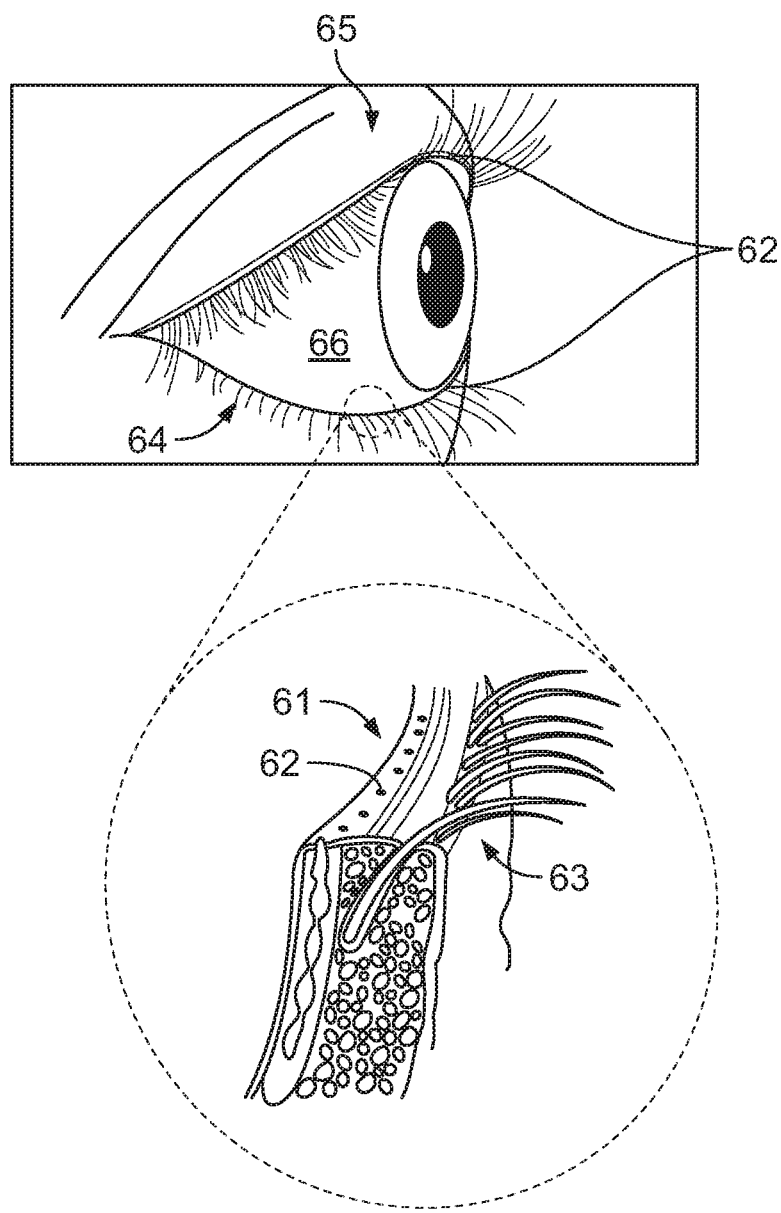
FIG. 1A is an illustration of an eye, including an enlarged view of a portion of an eyelid.

This present invention is capable of being embodied in various forms. The description below of several embodiments is made with the understanding that the present disclosure is to be considered as an exemplification of the claimed subject matter and is not intended to limit the attached claims to the specific embodiments illustrated. The headings used throughout this disclosure are provided for convenience only and are not to be construed to limit the claims in any way. Embodiments illustrated under any heading may be combined with embodiments illustrated under any other heading.

As used herein, the verb "to comprise" in this description, claims, and other conjugations are used in its non-limiting sense to mean those items following the word are included, but items not specifically mentioned are not excluded.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will also be understood that, although the terms first, second, etc. may be used herein to describe various elements, these elements should not be limited by these terms. These terms are only used to distinguish one element from another. Thus, a first element could be termed a second element without departing from the teachings of the present invention.

Some embodiments have been described in connection with the accompanying drawings. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

All existing subject matter mentioned herein (e.g., publications, patents, patent applications and hardware) is incorporated by reference herein in its entirety except insofar as the subject matter may conflict with that of the present invention (in which case what is present herein shall prevail).

The following patents and applications are incorporated by reference in their entireties: US Patent Publication No. 2019/0060115 filed Aug. 24, 2018, entitled "HANDHELD THERMAL THERAPY DEVICE", and US Patent Publication No. 2017/0273823, filed Mar. 23, 2017, and entitled "SYSTEM FOR PROVIDING INTERVAL THERMAL THERAPY."

The term "thermal energy applicator" "applicator" or the "Instrument" refers to a removable part that may be operatively connected and removed from the body of the device, the distal end (or wand head) of which comes into contact with the patient's tissue.

Embodiments of this application relate to a device that provides a heated surface for purposes of medical treatment or physical therapy. The device contains all the electronics, power conditioning, heating element, and a thermal energy applicator or Instrument. It may also contain a battery, either rechargeable or primary, in which case the device will operate with either internal battery power or power from a cord that is connected to an external power source. The operating voltage may be direct current, less than 30 VDC, typically 5-10 VDC.

The heating element may be a heater pad or heater blanket that contains resistive elements, a heater coil consisting of resistance wire, or any similar Joule heating device that converts electricity into heat using resistance. The heating element may also be a Thermoelectric Cooler (TEC), sometimes referred to as a Thermoelectric Module (TEM), otherwise known as a Peltier, or more descriptively a Peltier device assembly consisting of a plurality of alternating n-type and p-type semiconductors connected electrically in series, arranged such that their thermal output due to the Peltier effect is in parallel upon application of electrical current. The polarity applied to the TEC is such that the hot side is towards the Instrument part.

The device may also contain one or more temperature sensors, such as a thermistor, thermocouple or resistance temperature detector (RTD) for the purpose of measuring the heated surface temperature of the Treatment Instrument at or near the patient contact surface for feedback into the temperature control system and also in some embodiments for displaying to the user in real time. The device may also contain a thermal cutoff that acts as a fuse that is connected to the electronics in such a manner as to cause power to the heating element to be switched off, using a relay or other means, in the event of an electronics failure that causes excessive heating of the surface.

In an embodiment, the device may further comprise a thermal energy applicator or an Instrument. The Instrument may comprise an elongated body with at least one contact surface configured to communicate thermal energy between the applicator and the patient's tissue. The Instrument may be removed or connected to the body of the device, such that thermal energy may be conducted from the heating element to the Instrument. Engagement of the Instrument to the body of the device may be by levers or by other means. A heat flow adapter may be used to operatively connect the Instrument and the heating element to channel and distribute heat flow.

The Instrument may comprise at least one contact surface adapted for various purposes. The contact surface may be a single contact surface and oriented at different angles with respect to the body of the Instrument. The contact surface may be two contact surfaces and comprise other shapes or other additional functions. The contact surface may comprise paddles, debridement tools, thermal rollers, or unheated paddles. The paddles may be removeable, or may be made of plastic or elastomer material to reduce trauma inflicted on the tissue at treatment sites.

The Instrument part, which is the patient contact portion of the device, may be removable from the device. This allows the Instrument to be cleaned and sterilized independently. More significantly, this allows for numerous physical shapes and sizes of interchangeable Instrument parts to be used in the same device. Thus, for one particular use, such as Meibomian Gland Dysfunction treatment, the Instrument part may be of a particular size and shape suitable for contacting the eyelid. As another example, the part size and shape may be made suitable for treatment of another eye disorder based on where the area targeted for treatment is located and the geometric features best suited to treat that disorder.

In one embodiment, the device may be operated completely independently with respect to the number of times it is used and the durations of operation. The user simply turns the device on, selects a treatment, continues to select treatments until the therapy session is completed, and then turns the device off.

In a further embodiment, the device may be operated in a controlled manner, in that the number of times it is used and the durations of operation are recorded, internally within the device and/or in a separate computer, this separate computer being either a designated device that works with the handheld device or a non-specific, commercial computer that may exist in proximity to the device or exists on an external server. Communication between the device and external computers may range from a simple commercial method such as USB, Blue Tooth and Ethernet to more complex electronics such as is used in a smart phone. The record collected may enable a second party that owns, leases, or otherwise has a legal contract with the user to charge a fee based on the number of operating sessions, the durations of sessions, the combination of the sessions or duration of sessions or some other parameters.

In a further embodiment, the device is normally in an inactive state when powered on, waiting for an external communication. The user may then request or purchase a therapy session or sessions, this request being made using the communication methods aforementioned or through any other communication method. In this case, the separate computer may act as a host computer. The host computer may then determine if the request or purchase is authorized, and may potentially process the purchase transaction. The host computer may also be commanded to make the authorization by a third party. If authorized, then the host computer may send a communication to the device which allows it to be operated per the request or purchase. Upon completion of the session or sessions, the device may return to the inactive state.

The record of use may also be stored on a computer network, an internet web site, or the Cloud. Furthermore, the device may be programmed such that pre-authorization is required via the internet, Cloud, or other electronic communication methods before the device is able to be operated, thus enabling the aforementioned second party to charge a fee in advance for future therapy/treatment sessions.

Figure 1B:
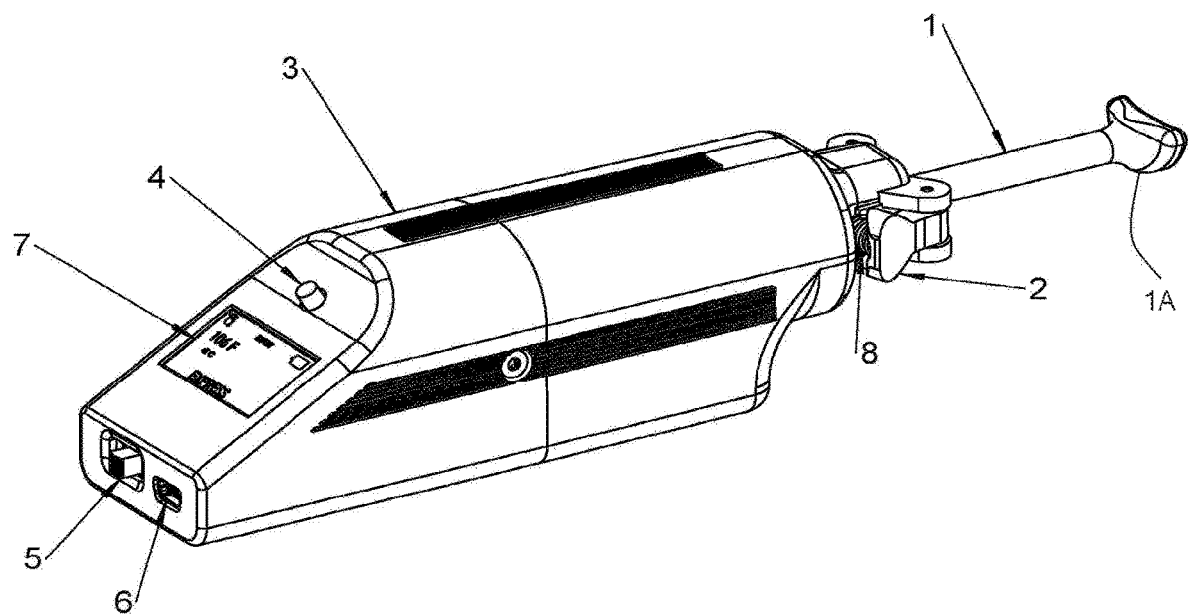
FIG. 1B shows an isometric view with the Warming Instrument installed.

Referring to FIG. 1B, the embodiment of the device 10 as shown comprises an instrument (1) detachably engaged to a body or housing (3). The instrument (1) is one of several types of interchangeable Instruments (or applicators) as described further herein.

The clinician installs and releases the instrument (1) to the housing (3) by squeezing the Lever parts (2).

FIG. 1B also shows a Selection button (4) to select the therapeutic mode, a Power switch (5) to turn the device on or off, a USB power connector which may also be used to update the software (6), a graphical Display (7), and Lever springs (8). Apart from the method of using spring-loaded levers, any other suitable means of engaging the parts together may be used.

Thermal Massage

The applicator or Instrument (1) shown in FIG. 1B is a Thermal Massage Instrument, made of a highly thermally-conductive material, which may have a shape that is designed to transmit heat to relatively large surface areas around the eye to, for example, prepare those areas for subsequent Debridement and Expression treatment. The Thermal Massage Instrument as shown comprises a contact thermal surface oriented orthogonally with respect to the body of the thermal energy applicator. Other angle and/or other shapes of the Thermal Massage Instrument are contemplated. A head (1A) of the instrument (1) is shown with an elliptical or bean-shaped profile and a slightly curved face serving to mate with the curvature of the eye. However, the shape and profile of the head may vary and the invention may feature other shapes.

In some embodiments, the head has a half moon shape, has rounded corners or is otherwise non-rectangular. The eyelid contacting surface is preferably concave, smooth or textured, or any combination of the aforementioned features.

Figure 1C:
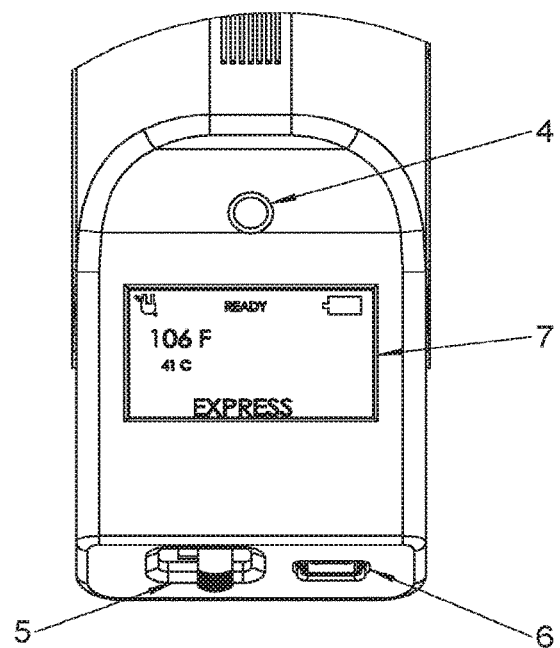
FIG. 1C shows an embodiment with a graphical Display.

FIG. 1C shows an embodiment with a graphical Display (7). This Display (7) can be LED, OLED, LCD or any other common type. It may contain a touchscreen to allow user interface with the display. The information it displays can consist of any useful data. In the case shown displayed is battery state, whether the device is plugged into an external power source or not, whether the temperature has stabilized to a steady state (READY), the currently measured temperature in two units (degrees Fahrenheit and degrees Celsius), and what mode the user has selected; these modes being Warming, Debridement or Expression. In some cases, LED indicators may be used instead of a graphical display. Where configured to do so, the Display may also display information on session length, the number of sessions used, or the mode of the sessions, among other information.

Alarms or alerts may be communicated to the user visually via a message on the graphical Display (7) which may blink, or visually via either dedicated discrete LEDs or a blinking of one of the existing LEDs in an embodiment wherein LEDS are used in place of a graphical display as the user interface. In addition, an auditory alarm such as a piezoelectric speaker may be built into the internal electronics to further supplement alarm or alert communication. Additionally, a timer may be built into the graphical display to assist the clinician user in delivering a specific therapy for a specific duration of time.

In the embodiment shown, a USB connector (6) is used to provide power to the device using a USB cord from any standard USB power-providing device. This can be a computer or a simple USB charger. The power cord may be used to charge an internal rechargeable battery, or in another embodiment may be used to power the device without need of an internal battery. Other connectors may be used to connect the device to a power source, either to charge an internal rechargeable battery or to provide power to the device.

Expression Applicator

FIG. 2A shows the device where the Instrument is a Thermal Expression Instrument, herein referred to as the Expression Instrument, with the Expression Instrument installed and fully closed. Shown are the thermally controlled part of the Expression Instrument (11) which is made of a highly thermally-conductive material, the indents in that part which engage the levers (10A); the unheated part of the Expression Instrument (12) which is made of a combination of a non-thermally-conductive material such as plastic for the main portion including the lever, and either a metallic, plastic or elastomer material for the patient contacting portion ("paddle") (40); and the Expression Instrument spring (13). The unheated part of the Expression Instrument (12) comprises an aperture (44) wherein the heated part (11) is extended therethrough. The heated and unheated parts contain matched paddles (40), (41) which compress tissue such as an eyelid together when the handle portion (43) of the unheated part is compressed by the user against the spring (13). The heated paddle (40) and the unheated paddle (41) come together upon compression by pressing of the handle (43). The paddles (40), (41) may have small, thin, flat, and smooth surfaces oriented such that they can press together and compress tissue without inflicting injuries to the tissue. The spring (13) loads the Expression Instrument (11) such that it is normally in the open position.

In another embodiment of the Expression Instrument, both paddles may be thermally controlled in order to apply heat equally to the tissue being compressed.

In certain patient cases, including the expression of meibomian glands, limiting the compression force imparted to the eyelid is important to reduce trauma during the expression procedure. The amount of force compressing the paddles together may be limited by limiting the stroke of the lever and utilizing the elastic characteristics of the unheated assembly to produce an effective spring force. In one embodiment, limiting of the stroke may be made to be user-adjustable with the addition of a suitable mechanism such as with a thumb screw (9) shown in FIG. 2B, where in this example the distance from the bottom of the thumbscrew to the Housing (3) is adjustable, thus limiting elastic deflection of the unheated assembly (12).

In another embodiment, the limit of the stroke may instead be fixed by designing a hard stop in the lever mechanism such as is shown in FIG. 2C whereby the effective spring force is the result of the tip of the lever portion of the unheated assembly (12) deflecting the distance 'A' until it contacts the Housing (3), this distance 'A' being predetermined to provide adequate maximum paddle compression force in general. Other compression force limiting mechanisms may be utilized instead of utilizing the elastic characteristics of the unheated assembly, for example by using a separate adjustable or non-adjustable compression, extension or torsional spring.

Debridement Applicator

Figure 3A:
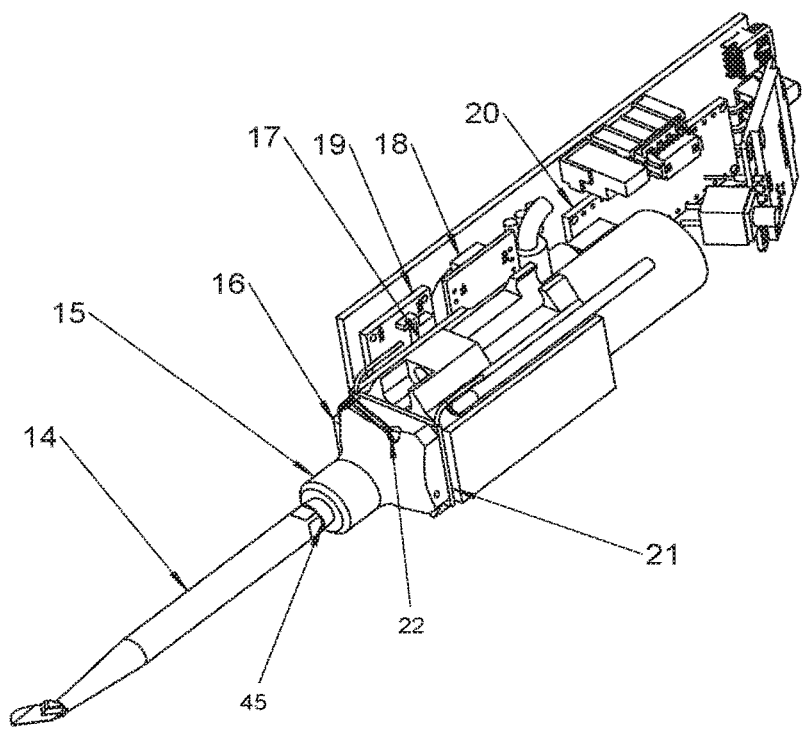
FIG. 3A shows an isometric view with the Debridement Instrument installed and the outer parts removed.

FIG. 3A shows a device and its elements in one embodiment with the outside housing parts hidden for facilitating understanding of the invention. The device is shown with a heated Debridement Instrument (14) installed. This Instrument part (14), which in embodiments, is preferably made of a highly thermally-conductive material, has a relatively thin and flat shape at the patient-contacting side with sharp edges as necessary for the debridement operation. In embodiments, the head of the debridement instrument has a hockey-stick shape and a sharp or blade-like edge. Other parts shown are a Heat Flow Adapter (15), made of a highly thermally-conductive material, that conducts heat from a heating element to the Debridement Instrument part, a Thermal Cutout device (16) that serves as a fuse in the event of thermal runaway (overheating) of the device, a Battery Housing (17), Battery Charging and Load Sharing electronics (18), Heater Power electronics (19), Microprocessor electronics (20), Heater Pad or TEC (21), and Temperature Sensor (22). If the heating element is a resistive Heater Pad, then the Battery Housing (17) is made of a material that is an electrical insulator, such as plastic. If the heating element is a TEC, then the Battery Housing (17) is made of a thermally-conductive material that is also probably electrically conductive, in which case the battery contained therein requires additional electrical insulation between it and the Battery Housing. The indents (45) for the lever ends, common with all the interchangeable ends with this embodiment of connection type, allow the Debridement Instrument part (14) to be retained in a plurality of rotational directions.

Figure 3B:
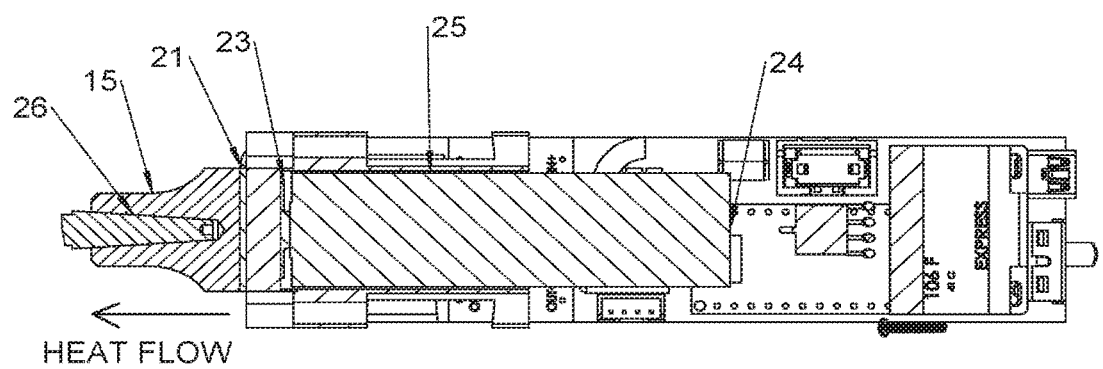
FIG. 3B is a cross-section view showing the battery and taper fit.

FIG. 3B shows a cross-section view of the aforementioned embodiment with an internal Battery (25). This battery (25) may be primary or rechargeable such as a Lithium-Ion or Nickel-Cadmium type. The direction of heat flow is from the heating element (21) through the Heat Flow Adapter (15) and into the Debridement Instrument part. Thermal interface material or thermal grease may be used to enhance thermal flow between thermally contacting parts. One pole of the Battery (25), in this case the Positive Pole (23) is embedded within the Battery Housing (17). The other pole of the Battery (25), in this case the Negative Pole (24), protrudes outside of the Battery Housing (17), allowing access to the Battery (25) for replacement. The thermal interface is a tapered angle fit (26) of small angle such that there is tight engagement of the two mating surfaces providing good surface contact for efficient heat energy transfer.

In addition to the tapered configuration (26) shown in FIG. 3B, the Instrument to Heat Flow Adapter (15) mating heat transfer surfaces could be a screw thread type engagement, a spring-loaded clamp type or other engagement. Also, the Heat Flow Adapter (15) part could be eliminated by designing the Instrument part with an interface to the heating element that replicates that of the Heat Flow Adapter part, and then by spring force or otherwise pushing the Instrument part and the heating element surfaces together directly. Although the latter could offer better heat transfer efficiency, the fragility and surface pressure requirements of the heating element must be taken into consideration.

Figure 3C:
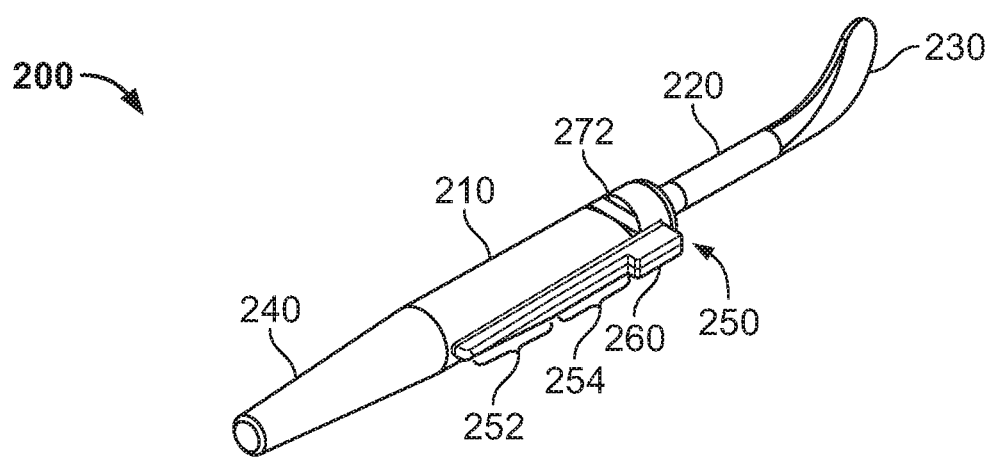
FIG. 3C shows an isometric view of a debridement instrument in accordance with another embodiment of the invention.

FIG. 3C is a perspective view of a one-piece debridement instrument (200) in accordance with another embodiment of the invention. The debridement instrument (200) shown FIG. 3C has a body (210), elongate neck (220), and distal head or tip (230). The distal tip (230) is shown having a sharp edge and an overall hockey stick-like profile. The tip (230) itself is both rigid, sharp and controllably heated as described herein.

The debridement instrument (200) shown in FIG. 3C also includes an elongate ridge or tongue (250) which, as described further herein, registers with a groove in the handpiece to align the instrument in a fixed orientation relative to the handpiece. In embodiments, the ridge (250) also has several different sub-regions including: a tapered region (252), a heat transfer region (254), and step or stop (260) to limit axial movement or depth into the handpiece.

Figure 3D:
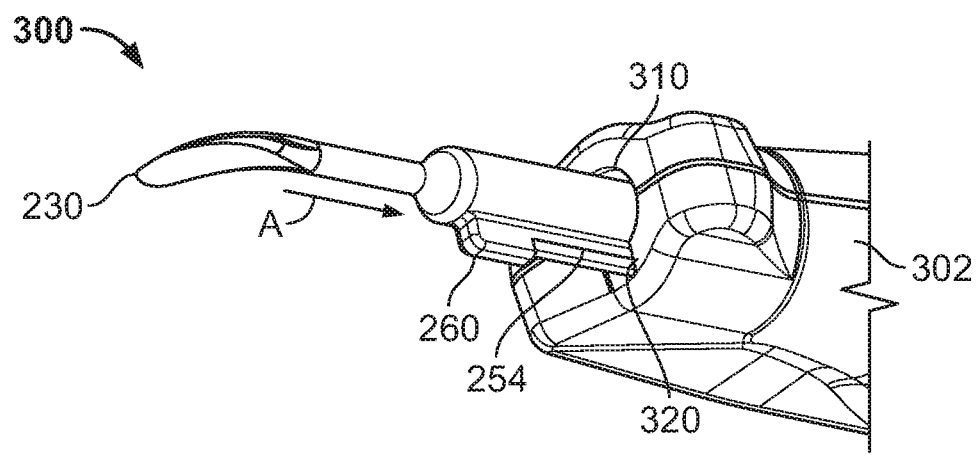
FIGS. 3D and 3E are enlarged partial views of the debridement instrument shown in FIG. 3C installed in a handle assembly.
Figure 3E:
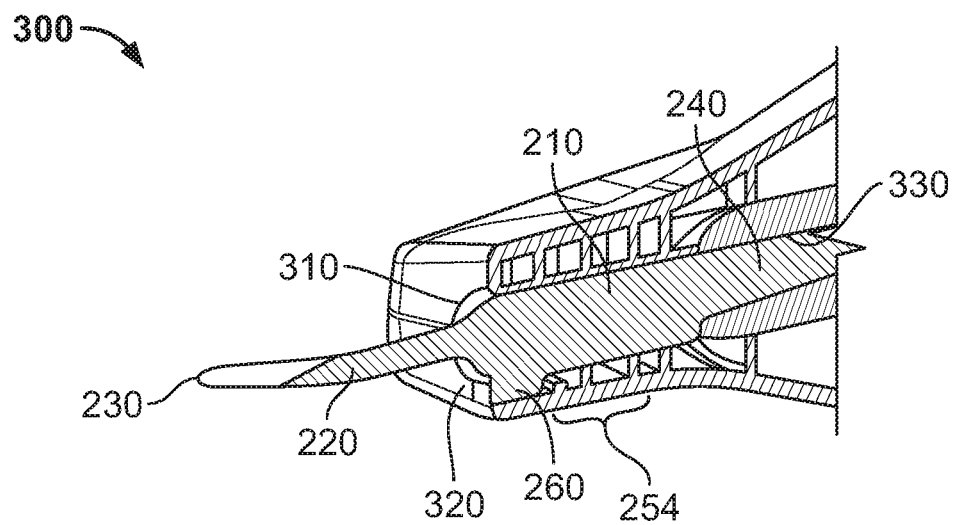

With reference to FIGS. 3D and 3E, the instrument (200) is shown being installed with a handpiece (300). Particularly, the body (210) of the instrument (200) is shown being advanced (A) into opening (310) in the handpiece. Ridge (250) is aligned with groove (320) similar to a key and keyhole in order for the instrument to be correctly advanced into the handpiece 300.

FIG. 3E shows a partial cross section of the instrument (200) fully installed in the housing (302) of the handpiece (300). Particularly, tapered proximal portion of the instrument is located in heat socket (330). Heat socket applies heat to the instrument as described herein.

Figure 3F:
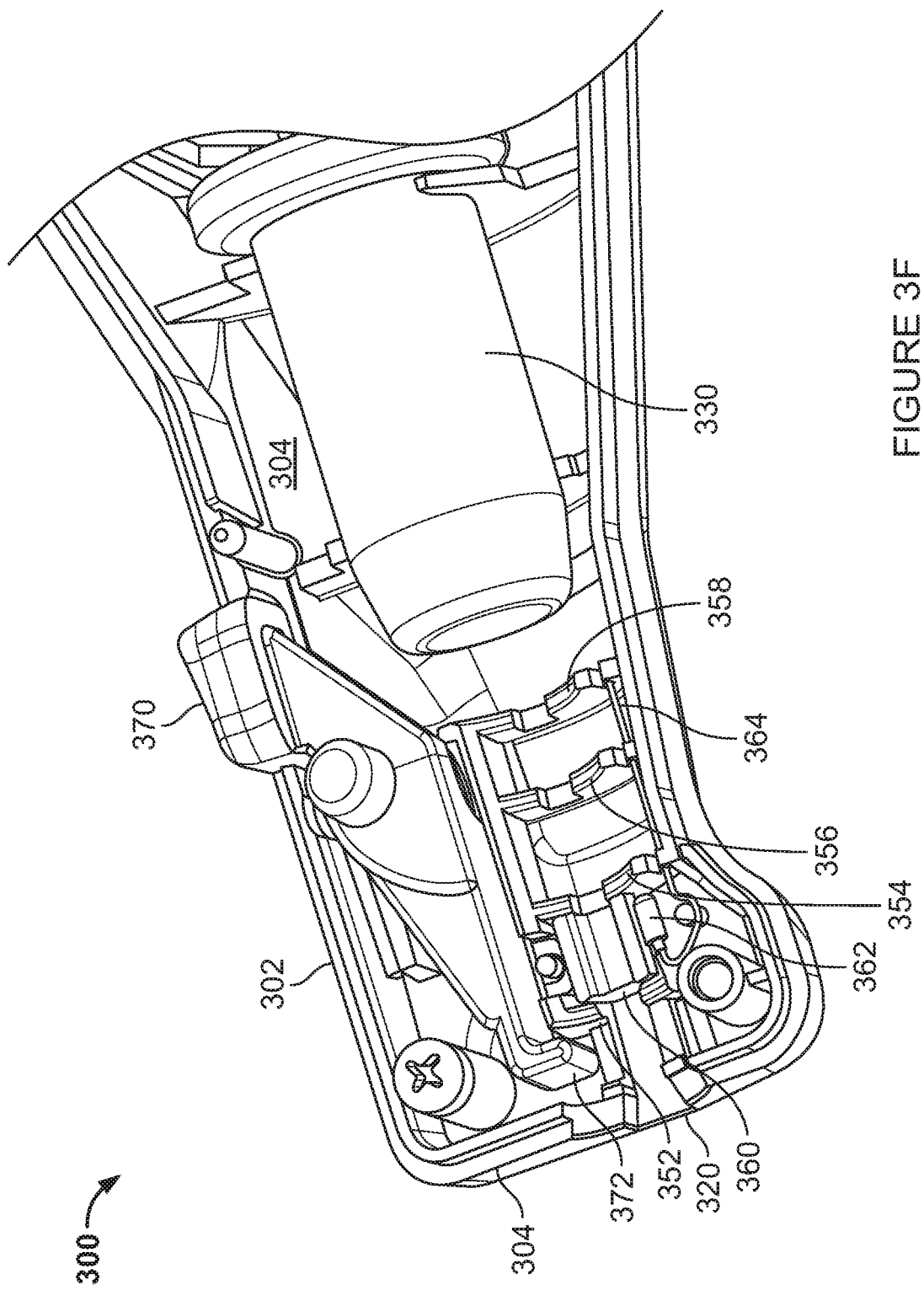
FIG. 3F is an enlarged partial view of the handle assembly shown in FIGS. 3D and 3E with its cover removed in accordance with another embodiment of the invention.

With reference to FIG. 3F, an enlarged partial view of a handpiece (300) is shown in accordance with an embodiment of the invention with part of its housing (302) removed for facilitating understanding of the invention. The handpiece (300) includes heat socket (330) which may be made of a thermally insulative material and holds a resistance heated wire coil therein to apply heat to the instrument base (240) when the instrument is installed.

A channel or groove (320) permits access to the instrument when the ridge (250) of the instrument is properly aligned. Struts or ribs (352, 354, 364, and 358) include guides or cutouts to align and support the ridge of the instrument when installed in the handpiece.

A push button (370) is shown linked to actuatable tab (372) for mating with a cutout or detent (272) in the instrument (200). Particularly, the lever (370) and tab (372) may be linked with a spring (not shown) to snap the tab into the cutout (272) of the instrument when the instrument is fully inserted. Depressing the button (370) disengages the tab (372) from the cutout, allowing the user to remove the instrument from the handpiece.

A discrete temperature capture assembly is shown and includes a temperature capture recess (360) fixed in the cavity (304) of the handpiece and in thermal connection to a temperature sensor (362). The combination of the capture recess (360) and temperature sensor allow temperature of the instrument to be measured as close as possible to the tissue contact surface or tip (230) of the instrument when installed. A wire (364) sends information from the sensor to a processor (not shown) in the handpiece for computing various steps in therapy methods in accordance with embodiments of the invention, discussed further herein.

The location of the temperature capture recess (360) may vary, and in preferred embodiments, it is distal to the heat generating element (e.g., heat socket (330)), and adjacent or as close as practical to the distal end (304) of the handpiece. In embodiments, the temperature capture recess is within 5 cm, and more preferably within 2.5 cm from the distal end of the handpiece or patient tissue. Without intending to being bound to theory, distancing the temperature capture recess from the heat element serves to more accurately measure the tissue contacting surface instead of merely measuring the temperature at the heating element or heat block used to transfer heat to an instrument which can be markedly different than the temperature at the working tip in contact with the patient.

In embodiments, the apparatus includes a processor and memory or storage device operable to determine a temperature signature (e.g., temperature as function of time) for the installed instrument by applying a set power or set power-time profile and recording or storing the measured temperature as function of time for the installed instrument. As described herein, in embodiments, the measured temperature arises from the temperature capture recess in close proximity to the instrument distal tip and not at the heating element.

Each type of instrument has a unique temperature signature due to its mass and thermal properties including heat capacity, and thermal conductivity. The temperature signature or characteristics of the temperature signature may be stored in the memory for a plurality of types of instruments. In embodiments, the apparatus comprises a database of types of instruments correlated with unique time-temperature profiles or time-temperature scores.

In embodiments, the processor is operable to determine the type of instrument installed based on the temperature signature, score, or characteristic of the temperature signature (e.g., the time for a max or steady state temperature to be reached).

In embodiments, the processor is operable to display, alert, or activate an instrument mode and heating scheme based on the type of instrument detected. Alternatively, or in combination, the candidate mode may be compared to the mode selected by the user, and if the modes do not match, an alert may be displayed or otherwise communicated to the user by the apparatus.

In embodiments, the apparatus computes or determines a max temperature and time based on the type of instrument installed and detected. Similarly, the processor can also compute or determine when an instrument is not installed, mis-installed, wrong instrument installed or instrument is absent based on the temperature feedback, namely, the temperature feedback reflects no increase with the application of power, or is otherwise intermittent or outside a threshold range. In such instances, the apparatus can alert the user via an alarm or display.

FIGS. 4A-4B show an embodiment with a warming instrument (1) installed. The warming instrument (1) in this embodiment has a half-moon shaped head and contact surface (1A) oriented primarily or approximately orthogonally to the body of the applicator. The surface is shown as slightly concave. In this embodiment, the head of the warming instrument includes only one contact surface adapted to treat one eyelid at a time. In other embodiments, the instrument may include a dual-head configuration to treat the upper and lower eyelids at the same time.

FIGS. 4C and 4D show the embodiment with the Debridement Instrument (14) installed. The head of the instrument (14) is shown having a golf-club or hockey-stick shape with a planar working portion at a 30-60 degree angle from the main shaft. The heated edge of the working portion is thin and adapted to scrape the eyelid posterior margin as described herein.

Figure 5A:
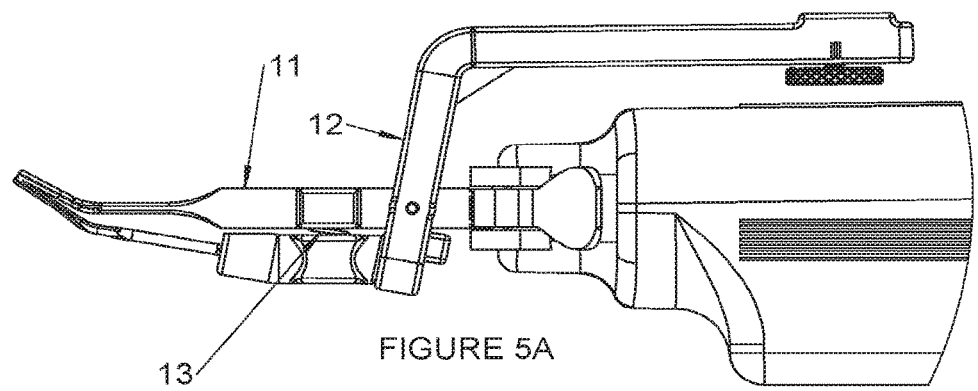
FIGS. 5A and 5B show the regular Expression Instrument installed.
Figure 5B:
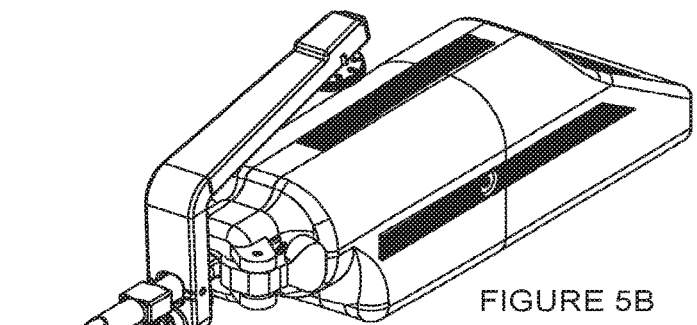

FIGS. 5A and 5B show the embodiment with the paddle enabled Expression Instrument (11) installed in the closed and open positions, respectively.

Figure 5C:
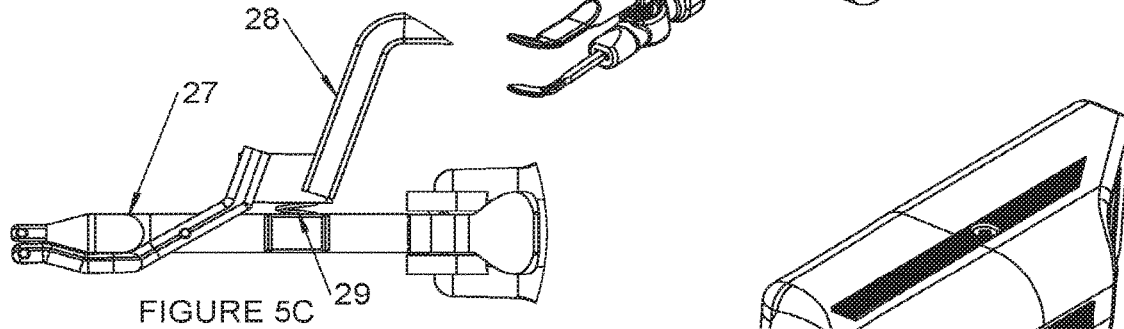
FIGS. 5C and 5D show the Roller Expression Instrument installed.
Figure 5D:
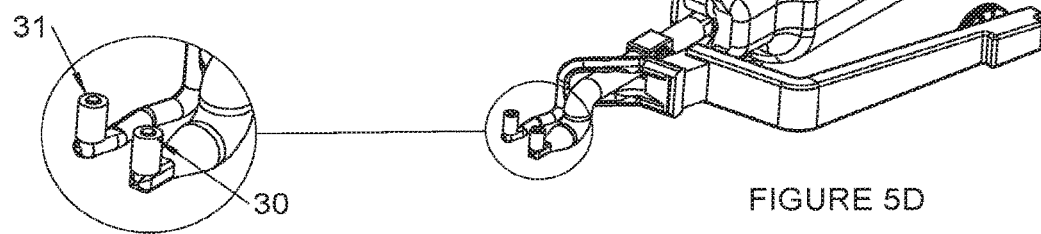

FIGS. 5C and 5D show an embodiment with a Roller enabled Expression Instrument installed in the closed and open positions, respectively. This Instrument comprises the Heated Roller Support (27) which is made of a highly thermally-conductive material, the Unheated Roller Support (28), the Spring (29), the Heated Roller (30) which is made of a highly thermally-conductive material and the Unheated Roller (31) which may or may not be made of a thermally-conductive material. The Non-heated Roller (or Unheated Roller) may be made of metal or soft material such as plastic or elastomer. The Heated Roller (30) is stationary while the Unheated Roller (31) moves by pressing of the Unheated Roller Support (28). Optionally, heat may be transferred to both Roller to deliver heat to both sides of the tissue being compressed between the two Heated Rollers. This Roller Expression Instrument operates in the same manner as does the regular Expression Instrument except it has rollers instead of paddles. The use of rollers reduces the friction forces and concentrates the compression force, resulting in a variation of the physical stress patterns of the expression treatment. The Roller Expression Instrument may yield better results than the regular Expression Instrument depending on patient characteristics.

In embodiments of the invention, one or both of the rollers are heated.

FIGS. 6A through 6D show an embodiment of an Expression Instrument that specifically uses a relatively soft material, such as plastic and or elastomer for the unheated paddle portion for the purpose of providing a softer, or "atraumatic" patient-contacting surface. Alternatively, the unheated paddle (or non-heated) may be made of metal, such as aluminum, among other materials. In an embodiment shown in FIG. 6A, the unheated paddle Instrument portion is integral with the rest of the unheated portion, such that the unheated portion (32) in this case is one single part constructed of the same plastic material or metal such as aluminum, although an elastomer may also be added to the paddle portion on the patient-contacting surface. An atraumatic roller Expression Instrument may be constructed in a similar manner.

FIGS. 6B through 6D show an embodiment in which there is a separate detachable unheated paddle part (34), made of plastic, elastomer, metal, or other soft material that is easily installable and removable from the main unheated lever assembly (33). In the example shown, the paddle part (34) mates to the main assembly (33) by virtue of an insert on (35) protruding into a cavity in the paddle part (34), whereby the parts are retained together by a snap-type mechanism (36) as shown in FIG. 6D. Other mechanisms to connect the detachable paddle part (34) to the main unheated lever assembly (33) may be used. The purpose of separate parts is to allow the parts to be constructed of different materials, optimally chosen for their functions. Also, the separate paddle portion may be made sterile and disposable rather than reusable. An atraumatic roller Expression Instrument may be constructed in a similar manner.

Figure 7A:
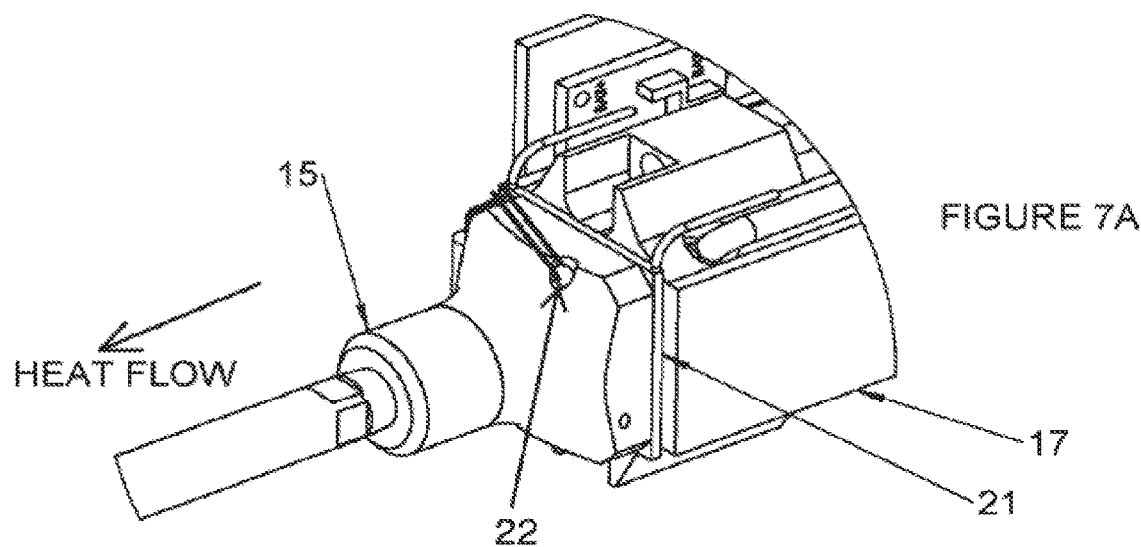
FIG. 7A shows the heating element as either a standard resistive heating blanket or a TEC.

FIG. 7A shows an embodiment with the heating element being either a resistive heating pad or a TEC (21), the material of the Battery Housing (17) and insulation requirements of the Battery being different depending on that choice. Heat is transmitted to the Instrument through the Heat Flow Adapter (15). A Temperature Sensor (22) is located at the Heat Flow Adapter (15) surface.

Figure 7B:
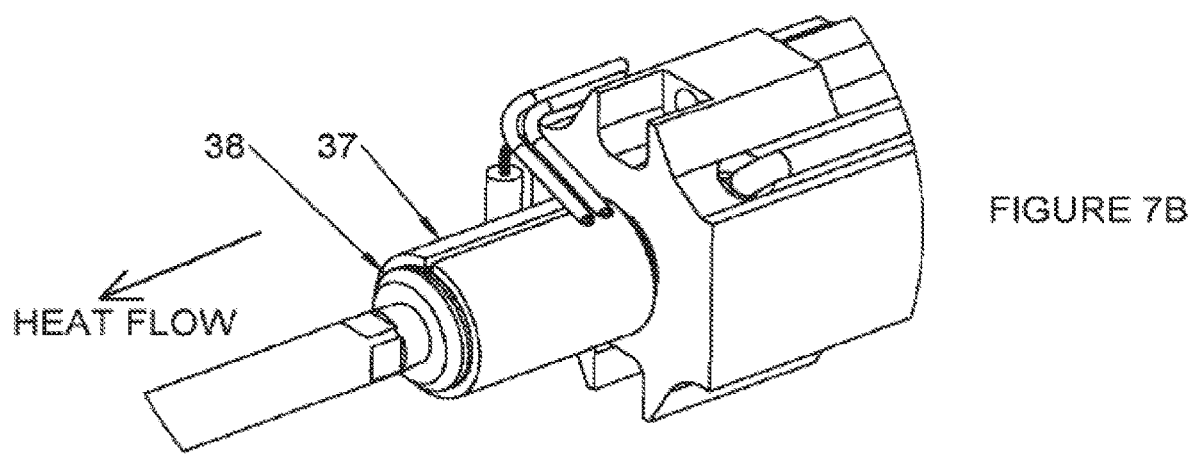
FIG. 7B shows the heating element as a resistive heating blanket.

FIG. 7B shows an embodiment where the heating element is a resistive Heating Blanket (37) wrapped around a differently designed Cylindrical Heat Flow Adapter (38). This Heating Blanket (37) may be made of heating wire or ribbon embedded into a silicone or polyimide substrate and may also contain the temperature sensor such as a thermistor.

Figure 7C:
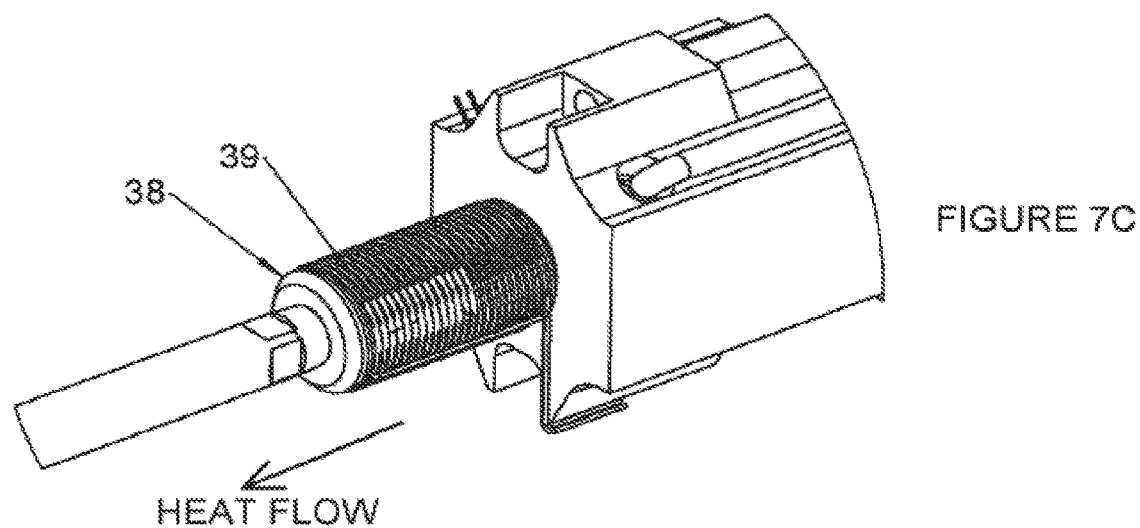
FIG. 7C shows the heating element as a coil of insulated resistance wire.

FIG. 7C shows an embodiment, which is the preferred heating embodiment, where the heating element is a Coil

(39) of resistance wire or ribbon such as Nickel-Chromium or other material designed to produce heat via Joule heating. The wire is either insulated with a thin layer of insulation, or the Heat Flow Adapter is pre-insulated, the bare (uninsulated) windings are spaced accurately apart so as not to short together, and a layer of insulation is applied after winding onto the Heat Flow Adapter. The wire insulation is necessary to prevent electrical shorting but is also thin at the inside surface to facilitate heat flow.

The Temperature Sensor (22) is shown located at the Heat Flow Adapter (15) surface, although in a further embodiment it may be instead located elsewhere such as, e.g., nearer to the patient-contacting surface of the Instrument part if it is desired to control the temperature at a location farther from the heating element and closer to where the heat is conducted to the patient. A benefit of this method is potentially greater temperature accuracy. However, this method presents more difficulty with temperature control due to thermal latency and is either more complicated if the sensor is built into the Instrument part given the electrical connection or is more cumbersome for the user if the sensor would need to be removed/replaced in order to remove/replace the Instrument part.

Methods of Construction

The devices described herein may be constructed variously. In embodiments, the device is constructed from a combination of off-the-shelf components and custom components. Examples of available off-the-shelf components include without limitation: microprocessor, PCBA (Printed Circuit Board Assembly), Battery charging and load sharing PCBA, Battery, graphical Display, LEDs, switches buttons, various basic PCBA components, connectors, H-bridge controller, inductors, capacitors, resistors, wires, fasteners, etc. Examples of custom parts include, without limitation, injection-molded plastic parts, the internal machined, cast or 3D-printed metal parts, and the machined or otherwise formed Heated Instrument parts.

In embodiments, the microprocessor operating system is an off-the shelf software and the firmware application can be is custom-written to carry out the functions described herein. If the system is completely analog-based with no microprocessor, then no firmware is required.

The metal parts that conduct heat may be constructed from any metal that has high thermal conductivity. Examples of these include several aluminum alloys such as alloys 6101 and 6063 which are relatively inexpensive and light and may be thinly plated with nickel, chrome, or other plating or coating to provide enhanced corrosion resistance. In embodiments, silver is may be used to obtain favorable heat transfer at the expense of higher material cost. Pure copper is an excellent material and may likewise be used at the expense of higher machining costs.

Parts may be assembled by hand and/or by automated means. Parts that are connected to each other are done so using any combination of the conventional mechanical fastening techniques (e.g., screws, pins, etc.). PCBAs are constructed per typical commercial manufacturing methods. Operations such as soldering are conventionally performed using standard tools.

Methods of Treatment

Embodiments of the invention include treatment methods, and particularly thermal treatment methods of Meibomian Gland Dysfunction and or Dry Eye Syndrome. Non-limiting exemplary protocols for treatment of Meibomian Gland Dysfunction and or Dry Eye Syndrome are described herein. Indeed, any of the steps described herein may be combined in any logical order except where such steps are exclusive to one another. Additionally, embodiments of the invention may include more or less steps than that described in the various embodiments (or protocols) recited herein except where such steps are recited in the appended claims.

Figure 8:
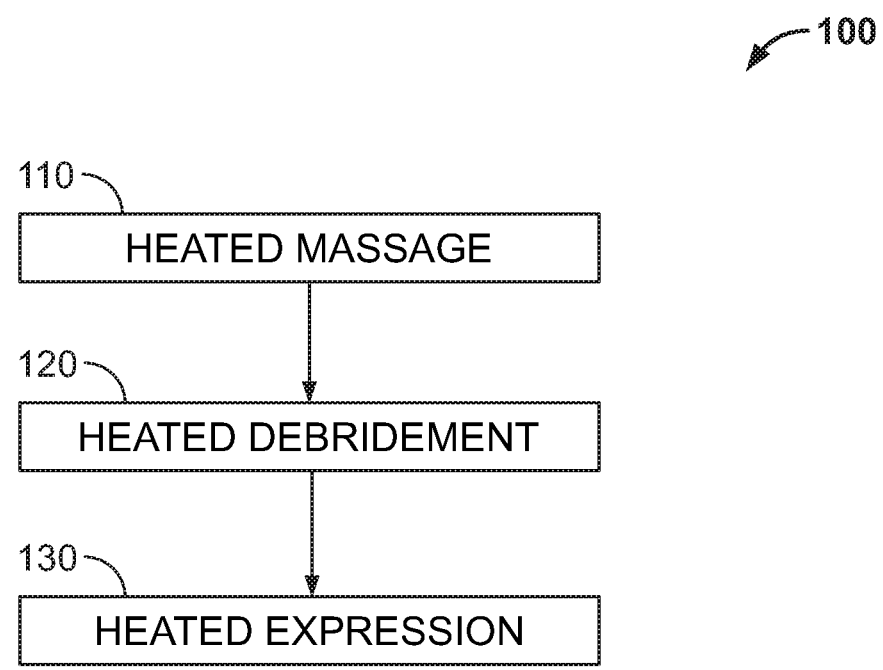
FIG. 8 is flow chart of a method for treating MGD in accordance with an embodiment of the invention.

With reference to FIG. 8, a multi-modality thermal method 100 for the treatment of Blepharitis, Meibomian Gland Dysfunction and Dry Eye Syndrome is shown.

Figure 9A:
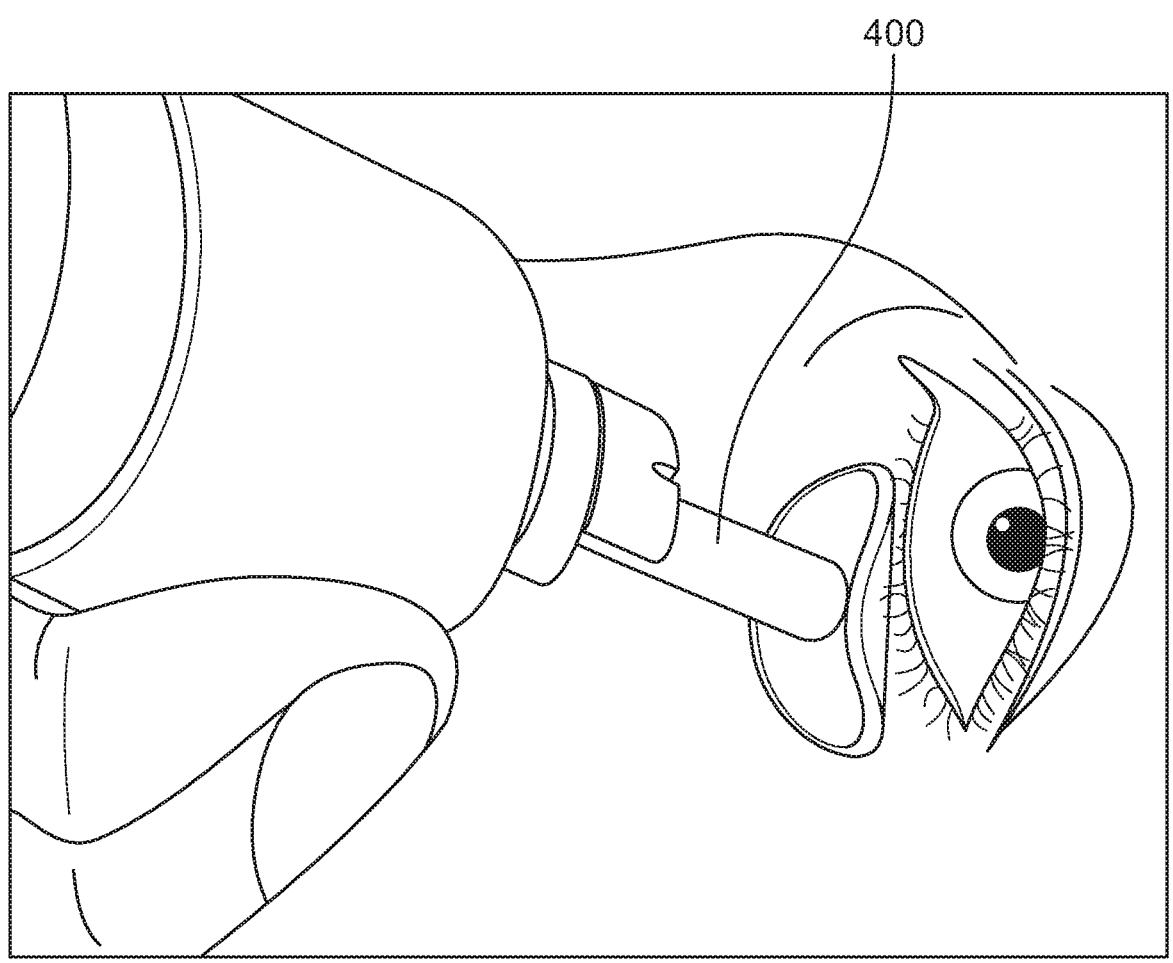
FIGS. 9A-9C are illustrations of thermal massage, thermal debridement, and thermal expression, respectively, in accordance with embodiments of the invention.

Step 110 states to thermally massage the eyelid. In embodiments, this step is performed by applying heat with light pressure to the surface of the eyelid. Preferably, an applicator (400) delivering heat and pressure is moved over the surface of the lid, preferably close to the eyelashes and preferably in a continuous side-to-side and/or circular motion as shown in FIG. 9A.

In other embodiments, the heating step can be performed using a heated compress. Heating the compress may be carried out in various ways such as by microwave, electronically via USB port and powered by a portable battery, or another energy source. A description of a heat compress is set forth in US Patent Publication No. 2019/0000664 to McMahon.

In embodiments, heat and pressure are applied to a single eyelid for 1-10 minutes, and more preferably 1-5 minutes, and most preferably about 1-3 minutes. In embodiments, heat and massage are applied for about 2 minutes.

The temperature for step 110 may vary and range from 40-50 degrees C., more preferably from 41-46 degrees C., and most preferably from 41-45 degrees C. In an embodiment, the heat therapy is about 44.5 degrees C.

Step 110 may be performed using various instruments. In a preferred embodiment, an applicator (1) having a single half-moon shape contact surface as set forth above in connection with FIG. 1B is used to perform step 110.

Figure 9B:
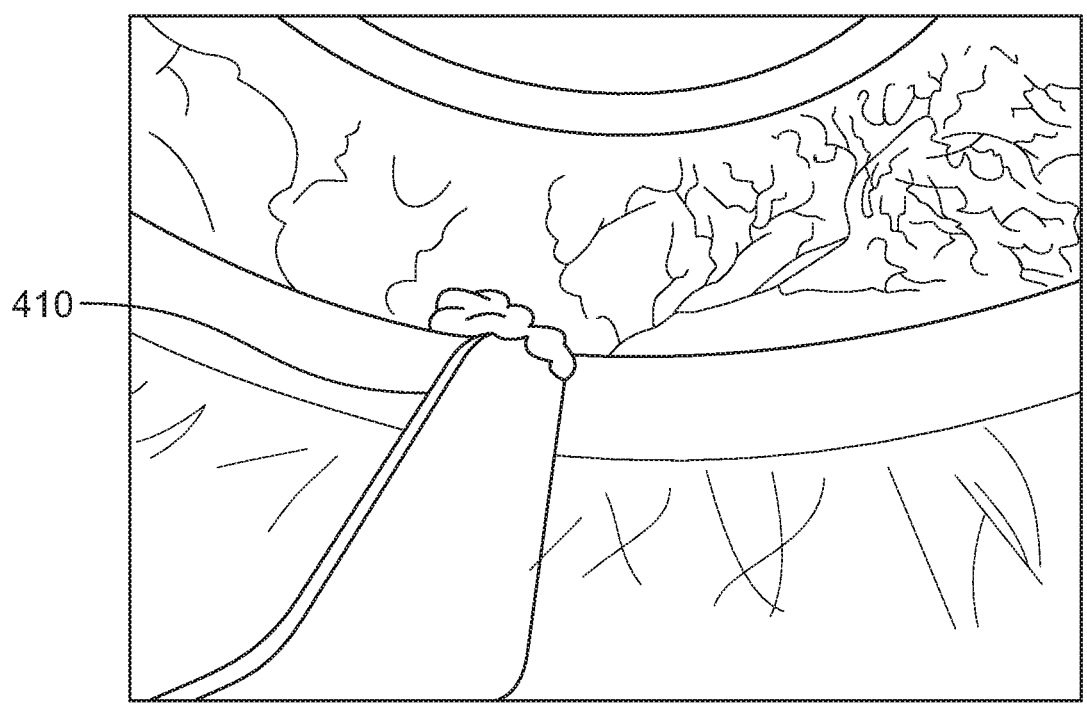

Step 120 states to thermally debride the eyelid. Preferably, an applicator (410) gently thermally debrides the lid margin to remove bacteria, biofilm, and "de-cap" Meibomian glands as shown in FIG. 9B. An example of an applicator for debriding the eyelid is shown in FIGS. 3A-3B.

This step may be performed by gently scraping the posterior lid margin with heat at temperatures ranging from 40-50 degrees C., more preferably from 41-45 degrees C., and most preferably about 42-44 degrees C., or about 42 degrees C.

The time duration to thermally debride each lid margin may range from 1-5 minutes, and more preferably about 1-2 minutes.

Figure 9C:
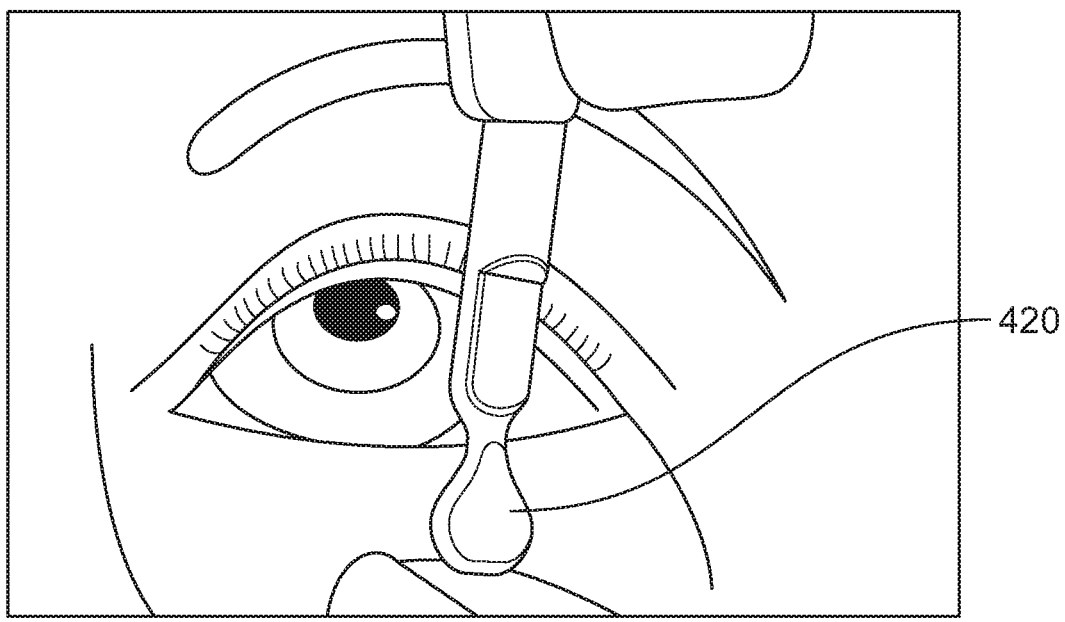

Step 130 states to thermally express the glands on the eyelid. Particularly, in embodiments, an applicator applies heat to the external lid while simultaneously applying pressure (optionally heated) to the internal side of the lid. In embodiments, with reference to FIG. 9C, the heat is applied with a smooth flat member (420) such as the heated paddles or rollers described above. With the opposing pressure to the eyelid, the eyelid can be depressed to express the fluid from the glands as shown in FIG. 9C. One may repeat the process until all the glands have been expressed.

This step may be performed by gently depressing with heat at a temperature ranging from 40-50 degrees C., more preferably from 42-46 degrees C., and most preferably about 42-44 degrees C., or about 43 degrees C. The device can be adapted to indicate when it has reached the target temperature (e.g., 43.3 degrees Celsius) on the heated surface (e.g., the external expressor paddle only).

In embodiments, the opposing forces during the expression step is performed semi-manually using the instrument. The physician receives tactile feedback enabling precise and safe control. The handle of the expression instrument described above may be gently squeezed and the physician obtains immediate tactile feedback on the pressure and can visually observe the degree of liquid expression.

In embodiments, the method includes limiting the opposing forces of the expression step both in pressure and gap. Particularly, in embodiments, an expressor applicator is physically limited to deliver less than or equal to 35 PSI of pressure to an eyelid of standard thickness. This serves to enable clinicians to express eyelids without concern of damaging the lid arising from excessive pressure.

In embodiments, thermal expression is applied to each eyelid for 1-4 minutes.

In the embodiment shown in FIG. 8, the step of debridement is performed prior to the step of expression. The step of heated massage is performed prior to the step of debridement. However, the order of the therapeutic steps may vary and the invention is only intended to be limited as recited in the appended claims.

In embodiments, the temperature applied to the eyelid sequentially increases with each step from heated massage, to debridement, to heated expression. Particularly, in embodiments, the temperature of the heated applicator surface may increase from about 40 (or 42) degrees C. during the initial heated massage to about 44-46 degrees C. in the debridement or expression steps.

Optionally, temperature is measured at a location spaced from the heat source and near the tissue contacting surface of the heated applicator, and the therapy mode is activated based on the measured temperature including a predetermined time temperature profile and the power is adjusted during treatment based on the measured temperature. However, it is to be understood that the invention is not intended to be so limited except as recited in the appended claims.

EXAMPLE

An example study of a method for treating Meibomian Gland Dysfunction (MGD) and Dry Eye Syndrome using a multi-modal thermal device (MMTD) in accordance with the invention is described herein.

The study included 37 adult patients with MGD and dry eye. All participants were enrolled in an open label, active treatment with the MMTD, where neither providers nor patients were blinded.

Inclusion criteria: to qualify for the study patients must have symptoms of dry eyes and MGD as determined by patient history and a Standard Patient Evaluation for Eye Dryness (SPEED) score of >12 or a Tear Breakup Time (TBUT) of <6 seconds, in at least one eye. Additional inclusion criteria included age >18, willingness to consent and comply with the study protocol and follow-up schedule.

Exclusion criteria included inability to consent or follow-up, MGD grade 3 atrophy, eyelid deformity or eyelid movement disorder, active corneal/conjunctival pathology or history of corneal/conjunctival pathology, active ocular allergy, use of cyclosporine eye drops, patients wearing contact lenses and use of warfarin or other anticoagulants.

Patient Evaluation: a comprehensive dry eye evaluation was conducted at the preliminary visit, including slit lamp evaluation of the tear lake (TBUT, corneal staining evaluation and SPEED Score). After the first 11 patients were enrolled, we added the collection of a Meibomian gland score (MGS) for the subsequent patients, for each eye. The eyelids were inspected with the aid of a Meibomian Gland Evaluator (MBE, TearScience®). The MGS was calculated by assessing the number of glands producing meibum multiplied by the quality of meibum secreted: clear=3, cloudy=2, inspissated=1. Follow-up examination was performed at thirty (30) days and included the same components as the initial exam: SPEED score, TBUT and MGS for each eye were recorded.

Overview of Treatment Protocol

Therapy with the device as described above in connection with FIGS. 1-3 was performed in an office setting, by a trained technician and/or optometrist. Topical anesthesia is achieved prior to using the device in a standard manner. Each treatment session was performed with the patient seated. Eyelids were treated one at a time.

The therapy for this study included: (A) 2 minutes of Thermal Heat Treatment using a Half-Moon shaped, concave, one-piece Heat Massage Instrument made of aluminum applied to each eyelid, followed by (B) 1-2 minutes of thermal lid debridement in which the one-piece debridement instrument was continuously heated while applied to the posterior lid margin and then (C) 1-2 minutes of Meibomian gland expression achieved by using a one-piece, thermally controlled expressor instrument, heated only on the external paddle applying heat to the external eyelid.

A) Thermal Massage of Eyelids:

Select the thermal massage applicator, and clean both the Thermal Massage head and the patient's eyelids with alcohol swabs prior to treatment. Coat the Thermal Massage head with ultrasound gel or other non-irritating lubricant (Coconut Oil, Vitamin E serum etc.) to enhance heat transfer and reduce friction of the wand head. Place the Heat Therapy proximal end (or tip) in the device by depressing the button on the underside of the device. Place the tip in securely and release the button. The device will heat the Thermal Massage tip to 44.5 Celsius. Depress the mode button for 2 seconds and a 2-minute timer will begin. Apply the Device Wand Head to the anterior surface of the eyelid (e.g., anterior surface 63 shown in FIG. 1A) with light pressure and move over the surface of the lid close to the eyelashes in a continuous side-to-side and circular motion. Continue treatment until a double beep is heard indicating that the selected program is complete (namely 2 minutes). Depress the mode button again for 2 seconds to start the timer and treat the other eyelid. Use a moist towelette and paper towels to wipe off the lubricant from the patient's eyes.

B) Thermal Debridement:

Select the debridement applicator. Place the Debridement tip in the Device. Select Debridement using the mode button. The device will show when the target temperature of 42.2 Celsius has been reached. Gently debride the posterior lid margin (e.g., the posterior edge 62 shown in FIG. 1A) to remove bacteria, bio-film and "de-cap" Meibomian glands. Remove the Debridement tip, by depressing the buttons on both sides of the handle and pull out on the tip. Debride for 1-2 minutes each lid.

C) Thermal Expression:

Remove the Debridement tip. Select the expression applicator. Next, place the Expressor in the Device. Hit the mode button and select Expression mode on the screen. The Device will indicate when it has reached the 43.3 Celsius target temperature on the external expressor paddle only. In the protocol for this example, only the exterior paddle is heated and should only be applied to the external lid. Apply the Expressor to the lid margin (heated paddle on external lid only) and depress to express glands. Move the Expressor paddles along the eye lid margin until all glands have been expressed. Additionally, the expressor is physically limited such that it can't deliver more than 35 PSI of pressure to an eyelid of standard thickness (e.g., 1 to 2 mm). This feature enables clinicians to express eyelids without concern of damaging the lid with excessive pressure. Thermal expression to each eyelid for 1-2 minutes until all Meibomian glands are expressed.

After each of the above-mentioned steps was completed, each eye had a post treatment Meibomian Gland Score (MGS) calculated.

Statistical analysis: the primary endpoints included change in SPEED score, change in TBUT and change in MGS. Descriptive statistics were utilized for demographics, SPEED score, TBUT and MGS. Conventional 2-sided t-testing was performed for continuous variables, with a $p<0.05$ being statistically significant. This analysis was performed with Google Sheets.

Figure 10:
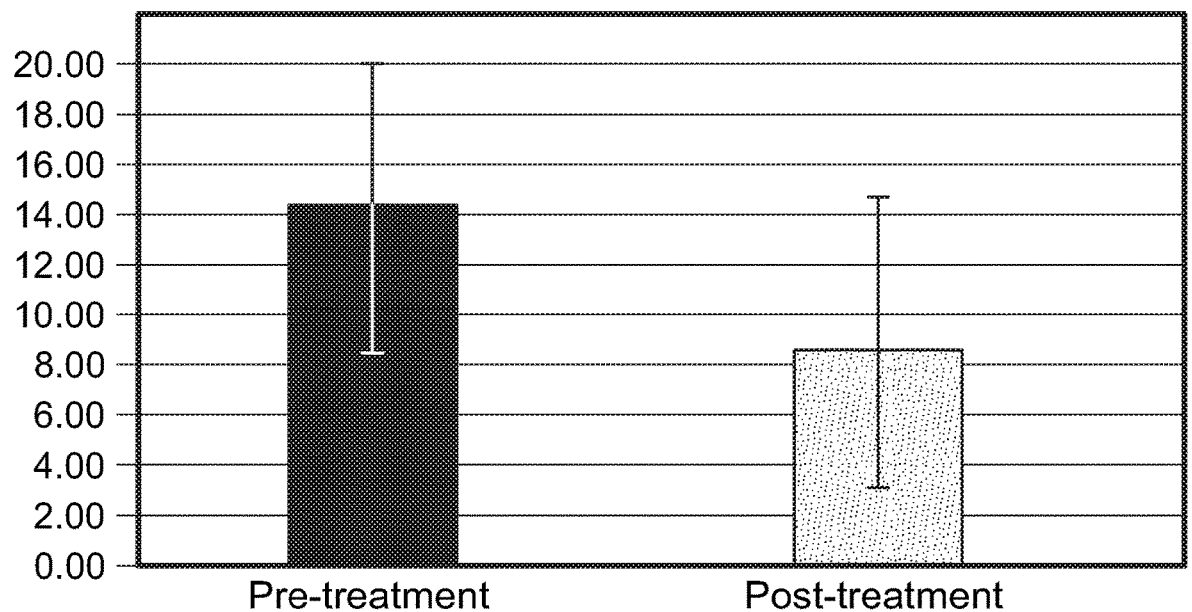
FIG. 10 is a graphical representation of SPEED Scores Before and After Treatment.
Figure 11:
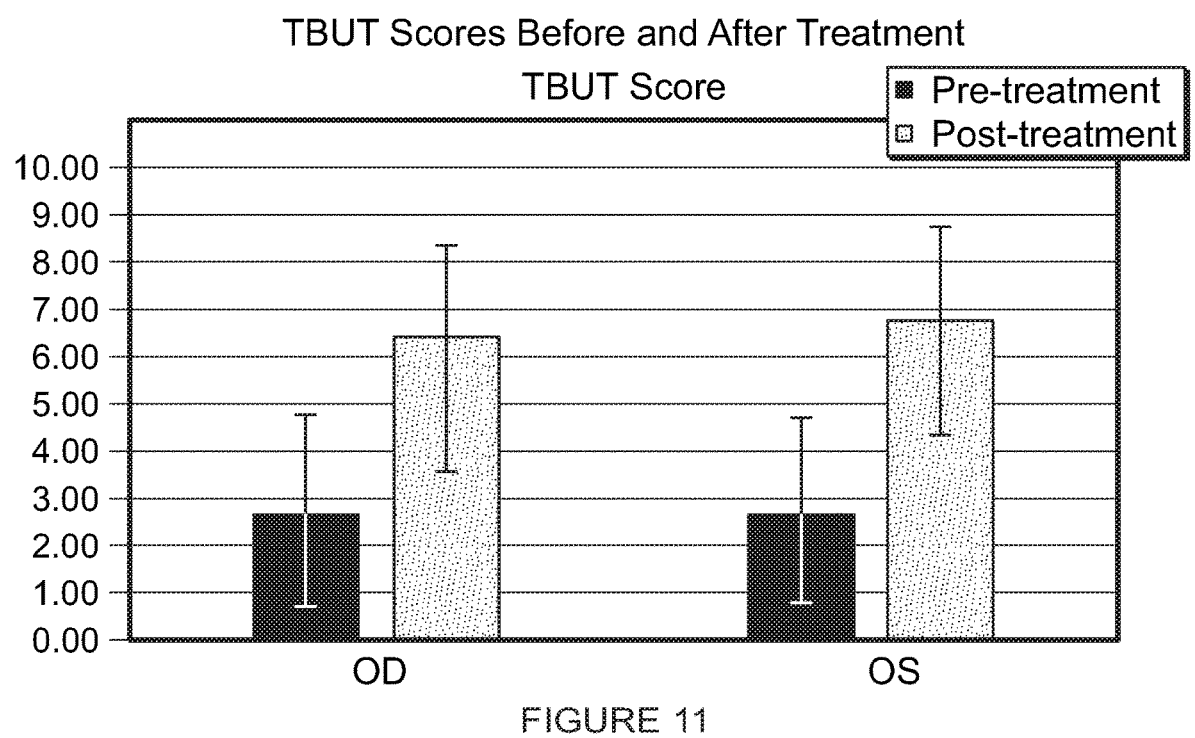
FIG. 11 is a graphical representation of TBUT Scores Before and After Treatment.
Figure 12:
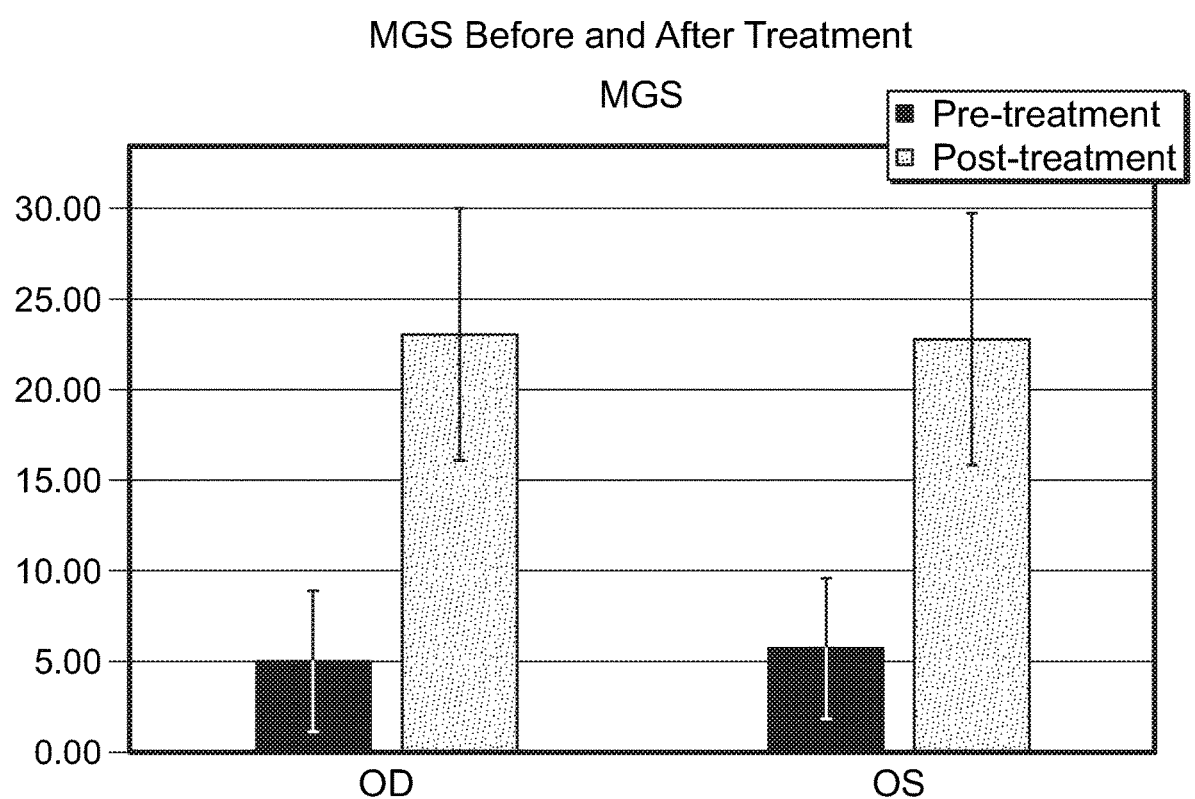
FIG. 12 is a graphical representation of MGS Before and After Treatment.

Results:

A total of 36 patients were treated with the device. Of these, 12 were men and 24 women with an average age of 57±14. Baseline demographics and patient variables are further discussed in Table 1. Statistically significant improvement (P<0.05) was noted in SPEED score (14.4±6 before, 8.6±5.6 after, FIG. 10) and TBUT (OD 2.7±2 before, 6.4±2.3 after; OS 2.7±2.1 before, 6.8±2.1 after, FIG. 11). A total of 26 patients had a MGS for both eyes and improvement was also statistically significant: OD 4.9±4 before, 23±7 after; OS 5.5±4.9 before and 22.7±7.7 after (FIG. 12). No adverse reactions were noted amongst any patients.

TABLE 1

Patient Demographics and Vision Characteristics

| Variable | N | Pre-treatment Mean ± SD | Post-treatment Mean ± SD |
|---|---|---|---|
| Age | 36 | 57 ± 14 | |
| Gender | M = 12, F = 24 | NA | |
| SPEED Score | 36 | 14.4 ± 6 | 8.6 ± 5.6 |
| TBUT OD | 36 | 2.7 ± 2 | 6.4 ± 2.3 |
| TBUT OS | 36 | 2.7 ± 2.1 | 6.8 ± 2.1 |
| MGS OD | 26 | 4.9 ± 4 | 23 ± 7 |
| MGS OS | 26 | 5.5 ± 4.9 | 22.7 ± 7.7 |

Discussion:

In the above described study 36 patients were treated with a MMTD to manage MGD. This was done in an open labelled, unblinded setting. A statistically significant improvement in SPEED score, TBUT and MGS for both eyes was noted after treatment. No adverse reactions were noted.

There are several advantages to a rapid, in-office treatment method in accordance with the above described therapy method. Foremost, the method can be delivered quickly in an outpatient setting, with minimal setup and training. Second, the method has a low-risk treatment, with no obvious adverse effects for the patients who have been treated. Third, adherence to therapy is likely to be much improved with a treatment that was reported to be comfortable and even pleasurable by patients, that may be needed periodically versus daily patient performed therapy. Finally, the above described method has shown significant improvement in objective measures of MGD, such as SPEED score, TBUT and Gland Scoring in our trial.

Conclusions. A single 10 minute treatment was effective at significantly improving dry eye symptoms secondary to MGD in adult patients. Additionally, a single treatment improved meibomian gland function and all measures of MGD in the adult patients treated.

Alternate Embodiments and Variations

Variations and modifications will occur to those of skilled in the art after reviewing this disclosure. The disclosed features may be implemented, in any combination and sub-combination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein.

For example, the various instrument tips described herein may be combined with the various body portions of the instruments in any way or manner except where such combinations are exclusive of one another. To this end, any of the expression instruments, debrider instruments, and massage instruments may include one or more elongate ridges or tongues for alignment of the tip and efficient temperature transfer to the temperature capture recess zone for measuring temperature of the tissue contact surface.

Additionally, the specific modes described herein (e.g., the exemplary therapy modes described in the Example) are intended to be exemplary, and the temperature and time profiles of a mode may vary except where recited in the appended claims. In embodiments, a mode is characterized by a target or set temperature for a type of therapy. In embodiments, a mode is characterized by the temperature and time duration of therapy. In embodiments, a mode is characterized by a temperature as function of time and the temperature can vary or be maintained at a constant value with time.

Additionally, in an alternate embodiment of the invention, thermal massage or heating of the outer surface of the lid may be performed with a wide range of different types of devices. Examples of heating devices include a dry eye heated compress. The compress may be heated by microwave, electronically, or otherwise. A description of a heat compress is set forth in US Patent Publication No. 2019/0000664 to McMahon. The compress may be heated by microwave, and gently set on the patient's eyelids for several minutes. In one embodiment, the heat compress is applied for about 5 minutes. However, in other embodiments as described herein, another type of heat application is applied, or the heat massage step may be omitted altogether.

What is claimed is:

1. A method for treating conditions of the eye comprising the following steps:
    detachably installing a proximal end of a thermally conductive debriding instrument in a receptacle of a hand-held sized heat-generating base assembly;
    debriding the eyelid margin while simultaneously applying heat to remove biofilm on and around the Meibomian Glands and decap the Meibomian Glands according to a predetermined thermal debride mode with the thermally conductive debriding instrument;
    replacing the thermally conductive debriding instrument in the receptacle of the base assembly with a thermally conductive massage instrument after completing the predetermined thermal debride mode;
    applying heat and pressure to thermally massage the exterior of the eyelid according to a predetermined heat massage mode with the thermally conductive massage instrument, wherein the heat and pressure to thermally massage is applied by the user holding and moving the base assembly to apply force of the thermally conductive massage instrument against the eyelid; and replacing the thermally conductive massage instrument in the receptacle of the base assembly with a thermally conductive expression instrument after completing the predetermined heat massage mode, the thermally conductive expression instrument comprising a paddle set including a heated paddle and an unheated paddle in pivotal engagement to the heated paddle; and performing thermal expression to the eyelid by:

(a) holding the handheld assembly by single-hand, (b) advancing the handheld assembly by single-hand to position the unheated paddle of the expression instrument under the eyelid of the patient and the heated paddle of the expression instrument over the eyelid, and (c) squeezing an arm member of the expression instrument to close the paddle set, thereby generating opposing forces to the interior and exterior of the eyelid while simultaneously applying heat from the heated paddle to express the meibum according to a predetermined thermal expression mode such that immediate tactile feedback on the pressure and visual feedback on the degree of liquid expression is obtained; and wherein the handheld-sized heat-generating base assembly is adapted to accept only one of said thermally conductive massage, debriding, and expression instruments at a time.

2. The method of claim 1, wherein during the performing thermal expression step, heat is applied only to the exterior side of the eyelid, and not applied to the inner side of the eyelid.

3. The method of claim 1, wherein during the performing thermal expression step, the pressure applied to the inner side of the eyelid is performed by an elastic member, deforming or conforming to some degree as increased pressure is applied to the inner eyelid thereby avoiding trauma to the eyelid.

4. The method of claim 1, wherein the predetermined thermal expression mode includes a set or target temperature for 1-2 minutes.

5. The method of claim 1, wherein the temperature of the instrument increases sequentially from the step of the applying pressure and heat to thermal massage to the step of performing thermal expression.

6. The method of claim 1, wherein each of the predetermined heat massage mode, thermal debridement mode, and thermal expression mode includes a set or target temperature for 1-2 minutes.

7. The method of claim 1, wherein each of the thermally conductive massage instrument, thermally conductive debriding instrument and thermally conductive expression instrument comprises a cylindrical body and an elongate ridge extending laterally from the cylindrical body that is alignable with at least one guide in the handheld-sized heat-generating base assembly in only one orientation.

8. The method of claim 7, further comprising limiting the axial distance based on a stop in the ridge, and automatically securing the instrument in the handheld-sized heat-generating base assembly when the instrument is advanced to a predetermined depth.

9. The method of claim 1, further comprising automatically determining an instrument type installed in the handheld-sized heat-generating base assembly based on a time temperature signature of the instrument installed therein.

10. The method of claim 9, further comprising activating one of said predetermined instrument modes based on the type of instrument detected.

11. The method of claim 1, further comprising measuring an effective temperature at a location on the instrument, and adjusting or compensating power delivered to a heating element in the base assembly to maintain a target therapeutic temperature.

12. The method of claim 11, wherein the effective temperature is measured via a temperature capture zone near the distal end of the handheld-sized heat-generating base assembly, and near the tip of the instrument when installed.

13. The method of claim 1, further comprising sterilizing the instruments.

14. The method of claim 1, wherein all the steps are performed in a single 10 minute treatment.

15. The method of claim 1, wherein the debridement instrument includes a sharp or blade-like edge.

16. The method of claim 1, further comprising limiting the pressure applied to the eyelid by the opposing paddles of the expression instrument by a stop on the expression instrument, wherein the stop is operable to cooperate with the arm and paddles to allow expression of liquified meibum from the glands but avoid trauma to the eyelids arising from excessive pressure.

* * * * *

UNITED STATES PATENT AND TRADEMARK OFFICE
CERTIFICATE OF CORRECTION

| | | |
|---|---|---|
| PATENT NO. | : 11,517,473 B2 | Page 1 of 1 |
| APPLICATION NO. | : 16/794646 | |
| DATED | : December 6, 2022 | |
| INVENTOR(S) | : David McMahon | |

It is certified that error appears in the above-identified patent and that said Letters Patent is hereby corrected as shown below:

On the Title Page

Assignee item (73), Line 1, delete "Hesith" and insert --Health--

Signed and Sealed this
Twenty-eighth Day of February, 2023

*Katherine Kelly Vidal*

Katherine Kelly Vidal
*Director of the United States Patent and Trademark Office*